US011202775B2

(12) United States Patent
Bamdad

(10) Patent No.: US 11,202,775 B2
(45) Date of Patent: Dec. 21, 2021

(54) METHODS FOR TREATMENT OF CANCER

(75) Inventor: Cynthia C. Bamdad, Waltham, MA (US)

(73) Assignee: MINERVA BIOTECHNOLOGIES CORPORATION, Waltham, MA (US)

( * ) Notice: Subject to any disclaimer, the term of this patent is extended or adjusted under 35 U.S.C. 154(b) by 148 days.

(21) Appl. No.: 12/238,362

(22) Filed: Sep. 25, 2008

(65) Prior Publication Data
US 2009/0069367 A1   Mar. 12, 2009

Related U.S. Application Data

(60) Provisional application No. 60/975,156, filed on Sep. 25, 2007.

(51) Int. Cl.
*A61K 31/437* (2006.01)
*A61P 35/00* (2006.01)
*B82Y 30/00* (2011.01)

(52) U.S. Cl.
CPC ............ *A61K 31/437* (2013.01); *B82Y 30/00* (2013.01)

(58) Field of Classification Search
CPC .............................. A61K 31/437; A61P 35/00
See application file for complete search history.

(56) References Cited

U.S. PATENT DOCUMENTS

| | | | |
|---|---|---|---|
| 5,314,908 A | 5/1994 | McAfee | |
| 7,767,689 B2 * | 8/2010 | Moon et al. | 514/292 |
| 2005/0272759 A1 | 12/2005 | Moon | |

FOREIGN PATENT DOCUMENTS

| | | |
|---|---|---|
| CN | 101 020 688 A | 8/2007 |
| WO | 03/020279 A2 | 3/2003 |
| WO | 2005/070930 A2 | 8/2005 |
| WO | WO 2005089764 A1 * | 9/2005 |
| WO | WO2007/053135 A1 | 5/2007 |

OTHER PUBLICATIONS

Fan et al. Pathology—Research & Practice, 2010, vol. 206, pp. 595-589.*
Nagai et al. Journal of Thoracic Oncology, Jan. 2006, vol. 1, Issue 1, pp. 46-51.*
Giatromanolaki et al. Clinical Cancer Research, 2000, vol. 6,mpgs. 1917-1921.*
International Search Report of PCT/US 08/77756, dated Jan. 9, 2009.
Wen, Ren, et al., "Preparation of 1-(3-indolyl)-1,2,3,4-tetrahydro-.beta.-carboline derivatives as antifungal and antitumor agents", XP002664848, Database CA [Online] Chemical Abstracts Service, Columbus, Ohio, US; Aug. 27, 2007, 2 pages.
Wei, W., et al., "Electrochemiluminescent detection of Mucin 1 protein and MCF-7 cancer cells based on the resonance energy transfer", The Analyst, vol. 137, No. 9, Jan. 1, 2012 (Jan. 1, 2012), p. 2101, XP55073539, ISSN: 0003-2654, DOI: 10.1039/c2an35059a.
Engelmann, K., et al., "MCF7 Side Population Cells with Characteristics of Cancer Stem/Progenitor Cells Express the Tumor Antigen MUC1", Cancer research, vol. 68, No. 7, Apr. 1, 2008 (Apr. 1, 2008), pp. 2419-2426, XP55073534, ISSN: 0008-5472, DOI: 10.1158/0008-5472.0AN-07-2249.

* cited by examiner

*Primary Examiner* — Samira J Jean-Louis
(74) *Attorney, Agent, or Firm* — Wilson Sonsini Goodrich & Rosati

(57) ABSTRACT

A method for treating or preventing cancer in a subject comprising administering a treatment effective amount of a chemotype 4 compound.

20 Claims, 6 Drawing Sheets
Specification includes a Sequence Listing.

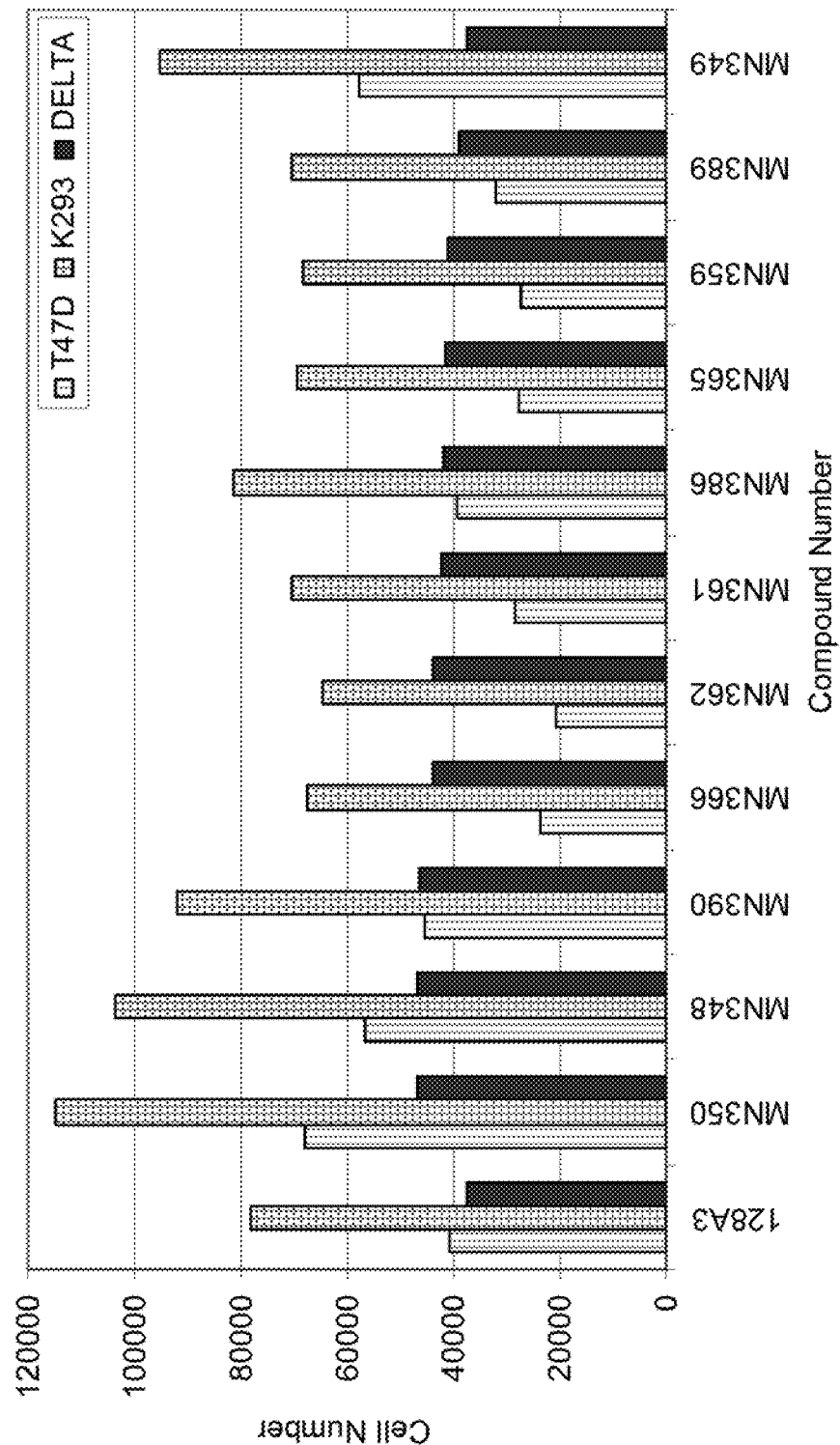

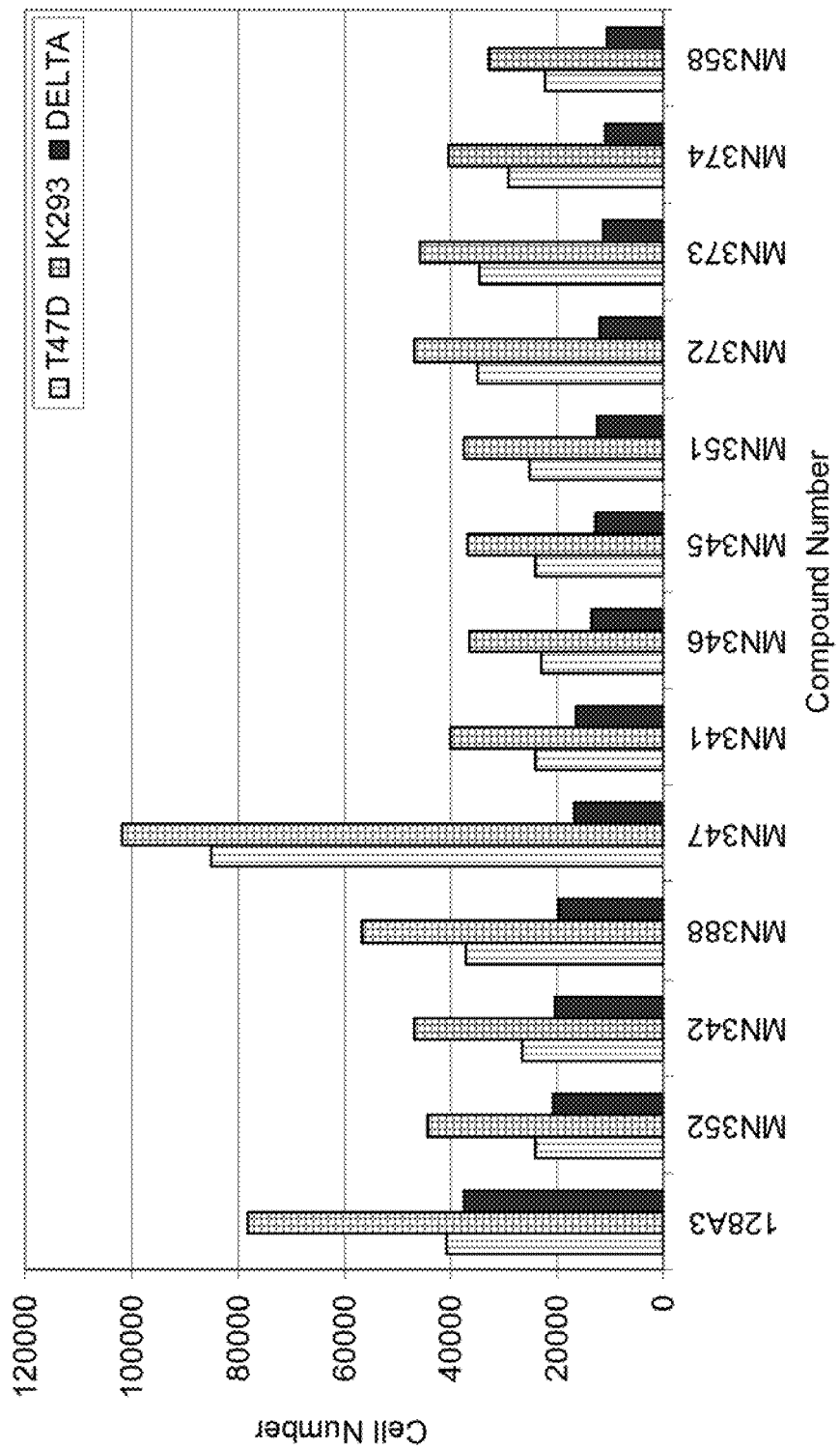

METHODS FOR TREATMENT OF CANCER

CROSS REFERENCE TO RELATED APPLICATIONS

The present application claims the benefit of priority to U.S. Provisional Patent Application Ser. No. 60/975,156, filed Sep. 25, 2007.

BACKGROUND OF THE INVENTION

1. Field of the Invention

This invention generally relates to methods and compositions for the treatment of cancers that are characterized by the presence of the MUC1 receptor and, in particular, to cancers that are characterized by the aberrant expression of the MUC1 receptor.

2. Description of the Related Art

All of the background information regarding the present application can be found in U.S. patent application Ser. No. 10/564,981, to Bamdad, which is incorporated by reference herein in its entirety regarding any background, or details of assay systems that are used in testing for certain anti-tumor activities.

As our knowledge of cancer grows, it has become increasingly clear that cancer is not a single disease, but rather a collection of diseases that share some common characteristics. Indeed, both the treatment and the characterization of cancers are changing rapidly as causative factors are identified at the molecular level and molecular "signatures" of sub-types of cancer are discovered. The treatment of breast cancers is being increasingly designed to target specific molecular signatures that are present in that particular cancer and in that particular patient. Excised breast tumors are often tested to determine whether they present, or present elevated levels, of estrogen receptor, progesterone-receptor, or more recently the Her2/neu receptor. The characterization of tumors at the molecular level guides the physician in the choice of possible treatments for a particular patient. Therapies that are molecularly tuned to a particular patient have had a measurable impact of cancer recurrence and survival. For example, patients with estrogen-receptor positive (ER+) and/or progesterone-receptor positive (PR+) cancers are typically treated with Tamoxifen for a period of up to 5 years. Tamoxifen, an estrogen analog, works by binding to and blocking the estrogen receptor's natural estrogen docking site. The recurrence rate of the cancer is dependent on several factors, but in general, patients with cancers that are both ER+ and PR+ fare better (efficacy ~70%) than those that are either ER+ or PR+ (efficacy ~30%), or ER−/PR− (efficacy ~10%). Herceptin is an antibody-based therapeutic that binds to and blocks Her2/neu receptor and has been shown to be effective against tumors that over-express this receptor. GLEEVEC® is a drug that treats chronic myeloid leukemia (CML). The drug inhibits the tyrosine kinase BCR-ABL, which is constitutively active in this type of cancer cell and initiates a cell growth signal. Blocking BCR-ABL and intercepting the growth signal halts proliferation; the lack of cell proliferation then induces the programmed cell death called apoptosis. Because this drug works on a target molecule that is aberrant in cancer cells, it has a very high cure rate and few if any side effects. Unfortunately, the mechanism that goes awry in CML represents only a small percentage of human cancers.

However, these results demonstrate that therapies that target specific molecules that are involved in the progression of cancer are more effective than earlier therapies that simply inhibit broad-spectrum cell growth. The new generation of cancer drugs such as HERCEPTIN® and GLEEVEC® and others being developed are called "smart" drugs because they home in on and disable specific molecules that are involved in cancer, or more often a particular type of cancer. Thus, in order to effectively determine which therapies are best for a particular patient, the patient's cancer can be characterized at the molecular level and treatments that act on specific aberrant molecules determined by the characterization can then be administered. Failure to characterize a cancer according to molecular signatures prior to treatment could cause the patient more harm than good. For example, by treating a patient with a drug that targets a particular molecule that is aberrant in some cancers, but not the type of cancer that the patient presents with, would constitute withholding appropriate treatment from that patient.

The MUC1 receptor is aberrantly expressed in a number of cancer types. MUC1 is a transmembrane glycoprotein found on the surface of epithelial cells. It has been reported that an estimated 75% of all human solid tumors aberrantly express the MUC1 receptor, including more than 90% of breast cancers and approximately 50% of prostate cancers. Other cancers in which the MUC1 receptor is aberrantly expressed include ovarian, colorectal, pancreatic, some lung cancers, and several others. For some time it has been known that in a healthy cell, the MUC1 receptors are clustered at the apical border, while in cancer cells, it appears to be uniformly expressed over the entire cell surface. This loss of clustering has been correlated to degree of cancer aggressiveness and patient prognosis. It is also known that the MUC1 receptor can be cleaved and shed from the cell surface. Shed receptor can be detected in the blood of healthy patients as well as breast cancer patients. Pregnant or lactating women have higher shed MUC1 levels in serum, while non-pregnant women, regardless of previous pregnancies, have shed MUC1 present in the serum, but at significantly lower levels. Elevated levels of shed MUC1 are only present in small percentage of patients with localized disease (Stage I). As a general rule, MUC1 shedding occurs more frequently as the cancer increases in stage, becoming metastatic. Tests that assess the serum levels of shed MUC1 are approved by the FDA for the detection of breast cancer recurrence in patients initially diagnosed with Stage II or III breast cancer. These tests utilize an antibody that recognizes the terminal repeat units of the MUC1 receptor. The number of tandem repeats of the MUC1 receptor varies from person to person and is not correlated to cancer. However, because a diagnostic test or tracking test must detect elevated levels of shed MUC1, the variable number of antibody epitopes makes it impossible to discriminate between elevated levels and increased antibody binding because that person's MUC1 contains a greater number of tandem repeat units. This variability in the number of repeat units from person to person introduces variability into the test and thus limits its utility for tracking a patient's response to therapy and prevents its use as a diagnostic. Therefore, what is needed is either an antibody that recognizes an epitope that is expressed a single time on each shed portion of the MUC1 receptor, or an antibody that recognizes an epitope that is present on shed MUC1 when cancer is present but not when MUC1 is shed in the normal state.

Proteases comprise another category of proteins that pharmaceutical companies are investigating as therapeutic targets. For example, protease inhibitors are effective treatments for HIV. Metalloproteases have been suggested as therapeutic targets of interest for a variety of conditions, including but not limited to cancers. Metzincins are a super-family of metalloproteins that includes three families of metalloproteases: MMPs, ADAMs, and ADAMTSs (ADAMS which contain one or more thrombospondin (TS) domains). These cleavage enzymes are produced as zymogens, which are not proteolytically active until a pro-peptide or pro-domain is cleaved or removed from its surface. This final processing step typically takes place at the cell surface. However, a subset of the metzincins are cleaved to generate the active enzyme in the golgi by furin or a furin-like enzyme. TIMPs (tissue inhibitors of metalloproteinases) are small proteins that bind to some metalloproteases and inhibit their proteolytic activity.

MMPs (matrix metalloproteinases) are a class of zinc-dependent endoproteases, wherein the metal is required for its activity. Six membrane-tethered MMPs, called MT-MMPs have been identified: MT1-MMP, MT2-MMP, MT3-MMP, MT4-MMP, MT5-MMP and MT6-MMP. All the MT-MMPs are processed to the proteolytically active form by furin. The MMPs were first named for their ability to degrade components of the extracellular matrix. Now, however, MMPs as well as other metalloproteases are emerging as a class of therapeutic targets for the treatment of inflammatory diseases and cancer. ADAM-17 is currently of pharmaceutical interest for the treatment of rheumatoid arthritis because it is required for the production of soluble TNFα.

Thus, there is a need to develop new and more accurate molecular signatures of cancers, and develop new therapeutic agents that act on those molecules that are specific to a type of cancer.

SUMMARY OF THE INVENTION

Certain embodiments of the present invention relate to compositions that are able to inhibit MUC1-related proliferative diseases, particularly cancers, involving inhibiting the portion of MUC1 that functions as a Growth Factor Receptor, cleavage of the full-length receptor to its tumorigenic form or interaction of the MUC1 receptor with its ligands, and methods for treating patients displaying symptoms of, or susceptible to MUC1-associated cancers by either inhibiting direct interactions or by inhibiting their expression. The subject matter of this application involves, in some cases, interrelated products, alternative solutions to a particular problem, and/or a plurality of different uses of a single system or article.

Several methods are disclosed herein of administering to a subject a composition for prevention or treatment of a particular condition. It is to be understood that in each such aspect of the invention, the invention specifically includes the composition for use in the treatment or prevention of that particular condition, as well as use of the composition for the manufacture of a medicament for the treatment or prevention of that particular condition. In some aspects of the invention, the invention also includes a pharmaceutically acceptable carrier.

The present invention includes methods of treatment of selected groups of patients. It is to be understood that all compositions described herein are useful or potentially useful for each described method.

Also included in certain embodiments of the present invention is a combinatorial approach in which structural features identified as characteristic of compositions effective for treatment at various disease stages are used as the basis for combinatorial synthesis of a wide variety of structural homologs, analogs, derivatives, enantiomers and functionally equivalent compositions thereof, for identification of a wide variety of compositions useful for treatment of MUC1-associated cancers. Thus, in one embodiment, the invention involves providing any one or more of the "chemotype 4 compounds" disclosed herein, performing a combinatorial synthesis resulting in a plurality of compositions. Then, one can perform an assay involving the plurality of the compositions to determine their effectiveness in cancer treatment, specifically, for example, treatment of cancers disclosed herein. The chemotype 4 compounds also can be altered using medicinal chemistry techniques.

Another aspect of the invention provides, in certain embodiments, a pharmaceutical preparation comprising a composition comprising any of the chemotype 4 compounds, and a pharmaceutically active carrier, including carbohydrates, lectins and/or lectin receptors. In one embodiment, compositions can comprise homologs, analogs, derivatives, enantiomers and functionally equivalent compositions thereof of chemotype 4 compounds. In all structures herein, atom locations, if unlabeled, are carbon with appropriate hydrogen(s). The invention also provides, in certain embodiments, a method involving promoting the prevention or treatment of MUC1-associated cancer via administration of any one or more of the compositions of the present invention and/or homologs, analogs, derivatives, enantiomers and functionally equivalent compositions thereof.

In another aspect, the invention provides a kit including any one or more of the compositions of the present invention and/or homologs, analogs, derivatives, enantiomers and functionally equivalent compositions thereof; and instructions for use of these compositions for treatment of cancer characterized by aberrant expression of MUC1.

In one aspect, the invention is defined, at least in part, by a method. In some embodiments of the invention, the method involves treating a human patient susceptible to or exhibiting symptoms of a cancer characterized by aberrant expression of MUC1 with any of the compositions disclosed herein. In one set of embodiments, the patient is susceptible to, but does not exhibit symptoms of, cancer characterized by aberrant expression of MUC1. In another set of embodiments, the patient exhibits symptoms of cancer characterized by aberrant expression of MUC1. In some embodiments of the method, the patient is not otherwise indicated for treatment for a cancer characterized by aberrant expression of a hedgehog protein.

In another aspect, the invention is directed to a method of making any of the embodiments described herein. In yet another aspect, the invention is directed to a method of using any of the embodiments described herein.

Aberrant expression of MUC1 can be observed by loss of clustering pattern of MUC1 on cell surface; or by membrane staining that uniformly covers a cell when contacted with anti-nat-PSMGFR or anti-var-PSMGFR peptide.

In another aspect, the invention is directed to the use of a compound that has dual moieties: MGFR binding moiety and metal chelating moiety. In this regard, the invention is directed to a method for treating or preventing MUC1-positive cancers comprising:

(i) testing a bodily sample for aberrant expression of MUC1; and (ii) treating the patient with a compound comprising a MGFR binding region and metal chelator group wherein the metal is zinc, magnesium or nickel.

The compound may be a metal-dependent protein inhibitor, wherein the metal dependent protein may be a member of the kinesin family, a kenesin spindle protein, or Costal2, or an enzyme that cleaves MUC1 such as matrix metalloprotease, particularly MT1-MMP or MMP-14, Furin, ADAM-17-TASE. The inhibitor may be TIMP, TIMP2 or TIMP3.

These and other objects of the invention will be more fully understood from the following description of the invention, the referenced drawings attached hereto and the claims appended hereto.

BRIEF DESCRIPTION OF THE DRAWING

The present invention will become more fully understood from the detailed description given herein below, and the accompanying drawings which are given by way of illustration only, and thus are not limitative of the present invention, and wherein;

FIGS. 1A-1D show effects of various compounds on MUC1-positive cells (T47D) and control cells (HEK293). Delta indicates maximum difference between the cell numbers observed in control versus cancer cells.

DETAILED DESCRIPTION OF THE INVENTION

Definitions

Figure 1A:
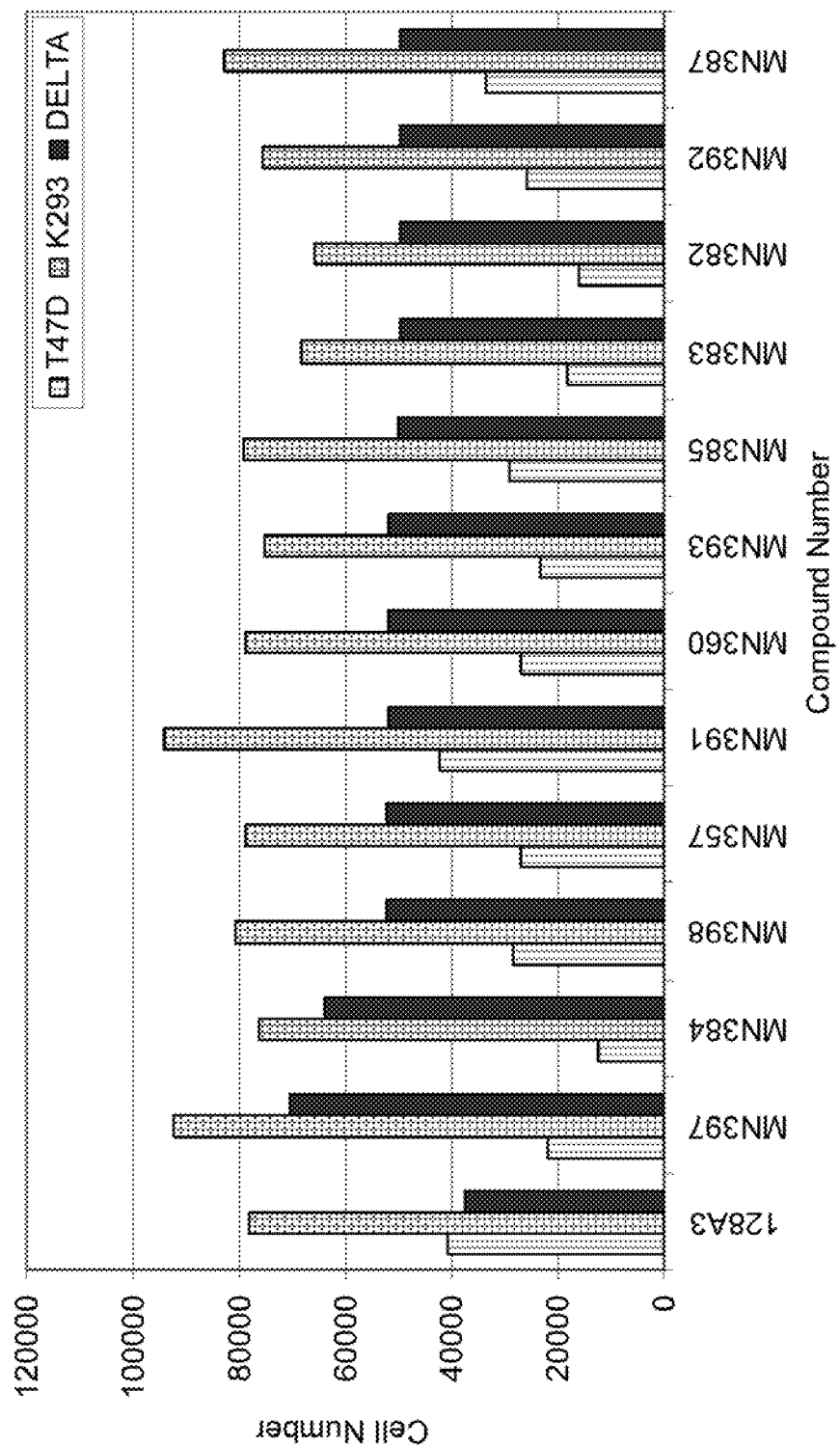
Figure 1C:
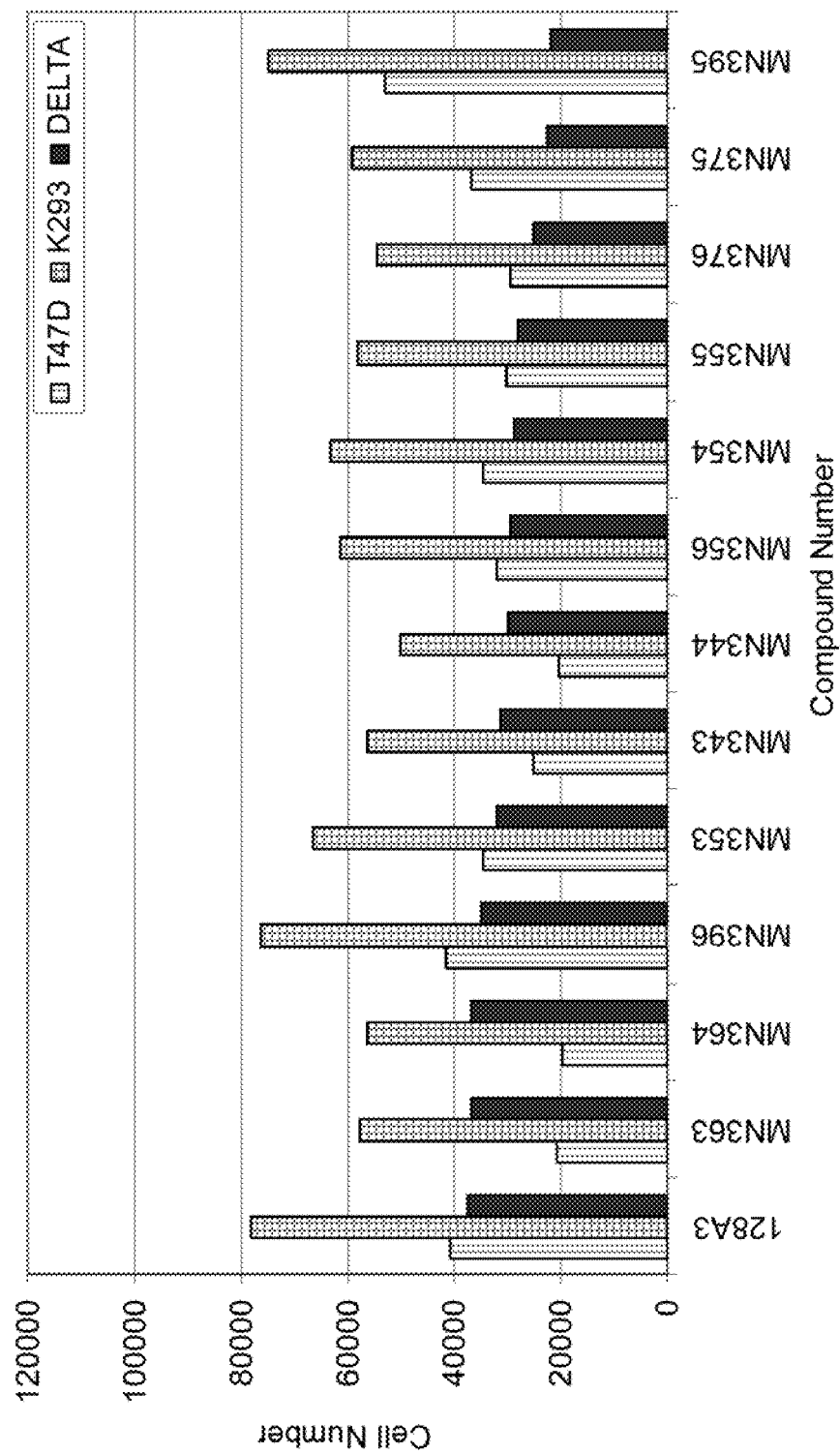

The term "MUC1 Growth Factor Receptor" (MGFR) is a functional definition meaning that portion of the MUC1 receptor that interacts with an activating ligand, such as a growth factor or a modifying enzyme such as a cleavage enzyme, to promote cell proliferation. The MGFR region of MUC1 is that extracellular portion that is closest to the cell surface and is defined by most or all by the primary sequence of MGFR (PSMGFR). The MGFR is inclusive of both unmodified peptides and peptides that have undergone enzyme modifications, such as, for example, phosphorylation, glycosylation, etc. Results of the invention are consistent with a mechanism in which this portion is made accessible to the ligand upon MUC1 cleavage at a site associated with tumorigenesis that causes release of the some or all of the IBR from the cell. MGFR is also known as MUC1*.

The term "Primary Sequence of the MUC1 Growth Factor Receptor" (PSMGFR) is a peptide sequence that defines most or all of the MGFR in some cases, and functional variants and fragments of the peptide sequence, as defined below. The PSMGFR is defined as SEQ ID NO:10 listed below in Table 1, and all functional variants and fragments thereof having any integer value of amino acid substitutions up to 20 (i.e. 1, 2, 3, 4, 5, 6, 7, 8, 9, 10, 11, 12, 13, 14, 15, 16, 17, 18, 19, or 20) and/or any integer value of amino acid additions or deletions up to 20 at its N-terminus and/or C-terminus. A "functional variant or fragment" in the above context refers to such variant or fragment having the ability to specifically bind to, or otherwise specifically interact with, ligands that specifically bind to, or otherwise specifically interact with, the peptide of SEQ ID NO: 10. One example of a PSMGFR that is a functional variant of the PSMGFR peptide of SEQ NO: 10 (referred to as nat-PSMGFR—for "native") is SEQ NO: 12 (referred to as var-PSMGFR), which differs from nat-PSMGFR by including an —SPY-sequence instead of the native—SRY— (see bold text in sequence listings). Var-PSMGFR may have enhanced conformational stability, when compared to the native form, which may be important for certain applications such as for antibody production. The PSMGFR is inclusive of both unmodified peptides and peptides that have undergone enzyme modifications, such as, for example, phosphorylation, glycosylation, etc.

The term "cancer", as used herein, may include but is not limited to: biliary tract cancer; bladder cancer; brain cancer including glioblastomas and medulloblastomas; breast cancer; cervical cancer; choriocarcinoma; colon cancer; endometrial cancer; esophageal cancer; gastric cancer; hematological neoplasms including acute lymphocytic and myelogenous leukemia; multiple myeloma; AIDS-associated leukemias and adult T-cell leukemia lymphoma; intraepithelial neoplasms including Bowen's disease and Paget's disease; liver cancer; lung cancer; lymphomas including Hodgkin's disease and lymphocytic lymphomas; neuroblastomas; oral cancer including squamous cell carcinoma; ovarian cancer including those arising from epithelial cells, stromal cells, germ cells and mesenchymal cells; pancreatic cancer; prostate cancer; rectal cancer; sarcomas including leiomyosarcoma, rhabdomyosarcoma, liposarcoma, fibrosarcoma, and osteosarcoma; skin cancer including melanoma, Kaposi's sarcoma, basocellular cancer, and squamous cell cancer; testicular cancer including germinal tumors such as seminoma, non-seminoma (teratomas, choriocarcinomas), stromal tumors, and germ cell tumors; thyroid cancer including thyroid adenocarcinoma and medullar carcinoma; and renal cancer including adenocarcinoma and Wilms tumor. Preferred cancers are; breast, prostate, lung, ovarian, colorectal, and brain cancer. Neoplasms in benign or malignant form are also considered within the purview of cancerous state.

The term "cancer treatment" as described herein, may include but is not limited to: chemotherapy, radiotherapy, adjuvant therapy, or any combination of the aforementioned methods. Aspects of treatment that may vary include, but are not limited to: dosages, timing of administration, or duration or therapy; and may or may not be combined with other treatments, which may also vary in dosage, timing, or duration. Another treatment for cancer is surgery, which can be utilized either alone or in combination with any of the aforementioned treatment methods. One of ordinary skill in the medical arts may determine an appropriate treatment.

As used herein, "bodily sample" refers to any body tissue or body fluid sample obtained from a subject. Preferred are body fluids, for example lymph, saliva, blood, urine, milk and breast secretions, and the like. Blood is preferred in certain embodiments. Samples of tissue and/or cells for use in the various methods described herein can be obtained through standard methods including, but not limited to: tissue biopsy, including punch biopsy and cell scraping, needle biopsy, and collection of blood or other bodily fluids by aspiration or other methods.

A "subject", as used herein, refers to any mammal (preferably, a human), and preferably a mammal that has a disease that may be treated by administering the inventive composition to a site within the subject. Examples include a human, non-human primate, cow, horse, pig, sheep, goat, dog, or cat. Generally, the invention is directed toward use with humans.

As used herein, a "MUC1-positive cancer" or a "MUC1*-positive cancer" refers to a cancer that is characterized by the aberrant expression of MUC1, wherein aberrant may refer to the overexpression of the MUC1 gene or gene product, or the loss of the normal expression pattern of MUC1 or MUC1* which, in the healthy state, is restricted to the apical border of the cell or the luminal edge of a duct or an increase in the amount of MUC1 that is cleaved and shed from the cell surface.

"Alkyl" refers to alkyl groups that do not contain heteroatoms. Thus the phrase includes straight chain alkyl groups such as methyl, ethyl, propyl, butyl, pentyl, hexyl, heptyl, octyl, nonyl, decyl, undecyl, dodecyl and the like. The phrase also includes branched chain isomers of straight chain alkyl groups, including but not limited to, the following which are provided by way of example: —$CH(CH_3)_2$, —$H(CH_3)(CH_2CH_3)$, —$CH(CH_2CH_3)_2$, —$C(CH_3)_3$, —$C(CH_2CH_3)_3$, —$CH_2CH(CH_3)_2$, $CH_2CH(CH_3)$ $(CH_2CH_3)$, —$CH_2CH(CH_2CH_3)_2$, —$CH_2C(CH_3)_3$, —$CH_2C(CH_2CH_3)_3$, —$CH(CH_3)$, —$CH(CH_3)(CH_2CH_3)$, —$CH_2CH(CH_3)_2$, —$CH_2CH_2CH(CH_3)(CH_2CH_3)$, —$CH_2CH_2CH(CH_2CH_3)_2$, —$CH_2CH_2C(CH_3)_3$, $CH_2CH_2C$ $(CH_2CH_3)_3$, —$CH(CH_3)CH_2$—$CH(CH_3)_2$, —$CH(CH_3)CH$ $(CH_3)CH(CH_3)_2$, —$CH(CH_2CH_3)CH(CH_3)CH(CH_3)$ $(CH_2CH_3)$, and others. Thus the phrase "alkyl groups" includes primary alkyl groups, secondary alkyl groups, and tertiary alkyl groups. Preferred alkyl groups include straight and branched chain alkyl groups having 1 to 12 carbon atoms.

"Alkylene" refers to the same residues as noted above for "alkyl," but having two points of attachment. Exemplary alkylene groups include ethylene (—$CH_2CH_2$—), propylene (—$CH_2CH_2CH_2$—), dimethylpropylene (—$CH_2C$ $(CH_3)_2CH_2$—), and cyclohexylpropylene (—$CH_2CH_2CH$ $(C_6H_{13})$—).

"Alkenyl" refers to straight chain, branched, or cyclic radicals having one or more carbon-carbon double bonds and from 2 to about 20 carbon atoms. Preferred alkenyl groups include straight chain and branched alkenyl groups and cyclic alkenyl groups having 2 to 12 carbon atoms.

Alkyl or alkenyl groups may be substituted. "Substituted alkyl" refers to an alkyl group as defined above in which one or more bonds to a carbon(s) or hydrogen(s) are replaced by a bond to non-hydrogen and non-carbon atoms such as, but not limited to, a halogen atom such as F, Cl, Br, and I; an oxygen atom in groups such as hydroxyl groups, alkoxy groups, aryloxy groups, and ester groups; a sulfur atom in groups such as thiol groups, alkyl and aryl sulfide groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as in trialkylsilyl groups, dialkylarylsilyl groups, alkyldiarylsilyl groups, and triarylsilyl groups; and other heteroatoms in various other groups. Substituted alkyl groups also include groups in which one or more bonds to a carbon(s) or hydrogen(s) atom is replaced by a higher-order bond (e.g., a double- or triple-bond) to a heteroatom such as oxygen in oxo, carbonyl, carboxyl, and ester groups; nitrogen in groups such as imines, oximes, hydrazones, and nitriles. Substituted alkyl groups further include alkyl groups in which one or more bonds to a carbon(s) or hydrogen(s) atoms is replaced by a bond to an aryl, heteroaryl, heterocyclyl, or cycloalkyl group. Preferred substituted alkyl groups include, among others, alkyl groups in which one or more bonds to a carbon or hydrogen atom is/are replaced by one or more bonds to fluoro, chloro, or bromo group. Another preferred substituted alkyl group is the trifluoromethyl group and other alkyl groups that contain the trifluoromethyl group. Other preferred substituted alkyl groups include those in which one or more bonds to a carbon or hydrogen atom is replaced by a bond to an oxygen atom such that the substituted alkyl group contains a hydroxyl, alkoxy, or aryloxy group. Other preferred substituted alkyl groups include alkyl groups that have an amine, or a substituted or unsubstituted alkylamine, dialkylamine, arylamine, (alkyl)(aryl)amine, diarylamine, heterocyclylamine, diheterocyclylamine, (alkyl)(heterocyclyl)amine, or (aryl)(heterocyclyl)amine group. Still other preferred substituted alkyl groups include those in which one or more bonds to a carbon(s) or hydrogen(s) atoms is replaced by a bond to an aryl, heteroaryl, heterocyclyl, or cycloalkyl group. Examples of substituted alkyl are: —$(CH_2)_3NH_2$, —$(CH_2)_3NH(CH_3)$, —$(CH_2)_3NH(CH_3)_2$, —$CH_2C(CH_2)$ $CH_2NH_2$, —$CH_2C(O)CH_2NH_2$, —$CH_2S(O)_2CH_3$, —$CH_2OCH_2NH_2$, —$CO_2H$. Examples of substituents of substituted alkyl are: —$CH_3$, —$C_2H_5$, —$CH_2OH$, —$OH$, —$OCH_3$, —$OC_2H_5$, —$OCF_3$, —$OC(O)CH_3$, —$OC(O)NH_2$, —$OC(O)N(CH_3)_2$, —$CN$, —$NO_2$, —$C(O)CH_3$, —$CO_2H$, —$CO_2CH_3$, —$CONH_2$, —$NH_2$, —$N(CH_3)_2$, —$NHSO_2CH_3$, —$NHCOCH_3$, —$NHC(O)OCH_3$, —$NHSO_2CH_3$, —$SO_2CH_3$, —$SO_2NH_2$, Halo.

As used herein, "Me" as in "4-Me" or "OMe" refers to a methyl group.

"Halogen" or "halo" refers to chloro, bromo, fluoro, and iodo groups. The term "haloalkyl" refers to an alkyl radical substituted with one or more halogen atoms. The term "haloalkoxy" refers to an alkoxy radical substituted with one or more halogen atoms.

"Cycloalkyl" refers to a mono- or polycyclic, heterocyclic or carbocyclic alkyl substituent. Representative cycloalkyl groups include cyclopropyl, cyclobutyl, cyclopentyl, cyclohexyl, cycloheptyl, and cyclooctyl and such rings substituted with straight and branched chain alkyl groups as defined above. Typical cycloalkyl substituents have from 3 to 8 backbone (i.e., ring) atoms in which each backbone atom is either carbon or a heteroatom. The term "heterocycloalkyl" refers herein to cycloalkyl substituents that have from 1 to 5, and more typically from 1 to 4 heteroatoms in the ring structure. Suitable heteroatoms employed in compounds of the present invention are nitrogen, oxygen, and sulfur. Representative heterocycloalkyl moieties include, for example, morpholino, piperazinyl, piperadinyl, and the like. Carbocycloalkyl groups are cycloalkyl groups in which all ring atoms are carbon. When used in connection with cycloalkyl substituents, the term "polycyclic" refers herein to fused and non-fused alkyl cyclic structures.

"Substituted heterocycle," "heterocyclic group," "heterocycle," or "heterocyclyl," as used herein refers to any 3- or 4-membered ring containing a heteroatom selected from nitrogen, oxygen, and sulfur or a 5- or 6-membered ring containing from one to three heteroatoms selected from the group consisting of nitrogen, oxygen, or sulfur; wherein the 5-membered ring has 0-2 double bonds and the 6-membered ring has 0-3 double bonds; wherein the nitrogen and sulfur atom may be optionally oxidized; wherein the nitrogen and sulfur heteroatoms may be optionally quarternized; and including any bicyclic group in which any of the above heterocyclic rings is fused to a benzene ring or another 5- or 6-membered heterocyclic ring independently defined above. The term "heterocycle" thus includes rings in which nitrogen is the heteroatom as well as partially and fully-saturated rings. Preferred heterocycles include, for example: diazapinyl, pyrryl, pyrrolinyl, pyrrolidinyl, pyrazolyl, pyrazolinyl, pyrazolidinyl, imidazoyl, imidazolinyl, imidazolidinyl, pyridyl, piperidinyl, pyrazinyl, piperazinyl, N-methyl piperazinyl, azetidinyl, N-methylazetidinyl, pyrimidinyl, pyridazinyl, oxazolyl, oxazolidinyl, isoxazolyl, isoazolidinyl, morpholinyl, thiazolyl, thiazolidinyl, isothiazolyl, isothiazolidinyl, indolyl, quinolinyl, isoquinolinyl, benzimidazolyl, benzothiazolyl, benzoxazolyl, furyl, thienyl, triazolyl, and benzothienyl.

Heterocyclic moieties can be unsubstituted or monosubstituted or disubstituted with various substituents independently selected from hydroxy, halo, oxo (CO), alkylimino (RN, wherein R is alkyl or alkoxy group), amino, alkylamino, dialkylamino, acylaminoalkyl, alkoxy, thioalkoxy, polyalkoxy, alkyl, cycloalkyl or haloalkyl. The heterocyclic groups may be attached at various positions as will be apparent to those having skill in the organic and medicinal chemistry arts in conjunction with the disclosure herein.

"Aryl" refers to optionally substituted monocyclic and polycyclic aromatic groups having from 3 to 14 backbone carbon or hetero atoms, and includes both carbocyclic aryl groups and heterocyclic aryl groups. Carbocyclic aryl groups are aryl groups in which all ring atoms in the aromatic ring are carbon. The term "heteroaryl" refers herein to aryl groups having from 1 to 4 heteroatoms as ring atoms in an aromatic ring with the remainder of the ring atoms being carbon atoms. When used in connection with aryl substituents, the term "polycyclic aryl" refers herein to fused and non-fused cyclic structures in which at least one cyclic structure is aromatic, such as, for example, benzodioxozolo (which has a heterocyclic structure fused to a phenyl group, i.e., naphthyl, and the like. Exemplary aryl moieties employed as substituents in compounds of the present invention include phenyl, pyridyl, pyrimidinyl, thiazolyl, indolyl, imidazolyl, oxadiazolyl, tetrazolyl, pyrazinyl, triazolyl, thiophenyl, furanyl, quinolinyl, purinyl, naphthyl, benzothiazolyl, benzopyridyl, and benzimidazolyl, and the like.

"Aralkyl" or "arylalkyl" refers to an alkyl group substituted with an aryl group. Typically, aralkyl groups employed in compounds of the present invention have from 1 to 6 carbon atoms incorporated within the alkyl portion of the aralkyl group. Suitable aralkyl groups employed in compounds of the present invention include, for example, benzyl, picolyl, and the like. Representative heteroaryls include, for example, imidazolyl, pyridyl, thiazolyl, triazolyl benzimidazolyl, benzothiazolyl, and benzoxazolyl.

"Biaryl" refers to a group or substituent to which two aryl groups, which are not condensed to each other, are bound. Exemplary biaryl compounds include, for example, phenylbenzene, diphenyldiazene, 4-methylthio-1-phenylbenzene, phenoxybenzene, (2-phenylethynyl)benzene, diphenyl ketone, (4-phenylbuta-1,3-diynyl)benzene, phenylbenzylamine, (phenylmethoxy)benzene, and the like. Preferred optionally substituted biaryl groups include: 2-(phenylamino)-N-[4-(2-phenylethynyl)-phenyl]acetamide, 1,4-diphenylbenzene, N-[4-(2-phenylethynyl)phenyl]-2-[benzyl-amino]-acetamide, 2-amino-N-[4-(2-phenylethynyl)phenyl]propanamide, 2-amino-N-[4-(2-phenyl-ethynyl) phenyl]acetamide, 2-(cyclopropylamino)-N-[-4-(2-phenylethynyl)-phenyl]-acetamide, 2-(ethylamino)-N-[4-(2-phenylethyny-1) phenyl]acetamide, 2-[(2-methyl-propyl) amino]-N-[4-(2-phenylethynyl)phenyl]acetamide, 5-phenyl-2H-benzo-[d]1,3-dioxolene, 2-chloro-1-methoxy-4-phenylbenzene, 2-[(imidazolylmethyl)-amino]-N-[4-(2-phenylethynyl)phenyl]acetamide, 4-phenyl-1-phenoxybenzene, N-(2-amino-ethyl)-[4-(2-phenylethynyl)phenyl] carboxamide, 2-{[(4-fluorophenyl)methyl]-amino}-N-[4-(2-phenylethynyl)-phenyl]acetamide, 2-{[(4-methylphenyl)methyl]amino}-N-[4-(2-phenyl-ethynyl-)phenyl]acetamide, 4-phenyl-1-(trifluoromethyl)benzene, 1-butyl-4-phenylbenzene, 2-(cyclohexylamino)-N-[4-(2-phenylethynyl)phenyl]acetamide, 2-(ethyl-methyl-amino)-N-[4-(2-phenyl-ethynyl)phenyl]acetamide-, 2-(butylamino)-N-[4-(2-phenyl-ethynyl)-phenyl]acetamide, N-[4-(2-phenylethynyl) phenyl]-2-(4-pyridylamino)-acetamide, N-[4-(2-phenylethynyl)phenyl]-2-(quinuclidin-3-ylamino) acetamide, N-[4-(2-phenyl-ethynyl)phenyl]pyrrolidin-2-ylcarboxamide, 2-amino-3-methyl-N-[4-(2-phenylethynyl)-phenyl]butanamide, 4-(4-phenylbuta-1,3-diynyl) phenylamine, 2-(dimethyl-amino)-N-[4-(4-phenylbuta-1,3-diynyl)phenyl]acetamide, 2-(ethylamino)-N-[4-(4-phenylbuta-1,3-di-ynyl)-phenyl]acetamide, 4-ethyl-1-phenylbenzene, 1-[4-(2-phenyl-ethynyl)-phenyl]ethan-1-one, N-(1-carbamoyl-2-hydroxypropyl)[4-(4-phenylbuta-1, 3-di-ynyl)-phenyl]-carboxamide, N-[4-(2-phenylethynyl) phenyl]propanamide, 4-methoxy-phenyl phenyl ketone, phenyl-N-benzamide, (tert-butoxy)-N-[(4-phenylphenyl)-methyl]-carboxamide, 2-(3-phenyl-phenoxy)ethanehydroxamic acid, 3-phenylphenyl propanoate, 1-(4-ethoxyphenyl)-4-methoxybenzene, and [4-(2-phenylethynyl)phenyl] pyrrole.

"Optionally substituted" or "substituted" refers to the replacement of hydrogen with a monovalent or divalent radical. Suitable substitution groups include, for example, hydroxyl, nitro, amino, imino, cyano, halo, thio, sulfonyl, thioamido, amidino, imidino, oxo, oxamidino, methoxamidino, imidino, guanidino, sulfonamido, carboxyl, formyl, alkyl, haloalkyl, alkyamino, haloalkylamino, alkoxy, haloalkoxy, alkoxy-alkyl, alkylcarbonyl, aminocarbonyl, arylcarbonyl, aralkylcarbonyl, heteroarylcarbonyl, heteroaralkyl-carbonyl, alkylthio, aminoalkyl, cyanoalkyl, aryl and the like.

The substitution group can itself be substituted. The group substituted onto the substitution group can be carboxyl, halo, nitro, amino, cyano, hydroxyl, alkyl, alkoxy, aminocarbonyl, —SR, thioamido, —SO$_3$H, —SO$_2$R, or cycloalkyl, where R is typically hydrogen, hydroxyl or alkyl.

When the substituted substituent includes a straight chain group, the substitution can occur either within the chain (e.g., 2-hydroxypropyl, 2-aminobutyl, and the like) or at the chain terminus (e.g., 2-hydroxyethyl, 3-cyanopropyl, and the like). Substituted substituents can be straight chain, branched or cyclic arrangements of covalently bonded carbon or heteroatoms.

Certain of the compounds of the invention comprise asymmetrically substituted carbon atoms. Such asymmetrically substituted carbon atoms can result in the compounds of the invention comprising mixtures of stereoisomers at a particular asymmetrically substituted carbon atom or a single stereoisomer. As a result, racemic mixtures, mixtures of diastereomers, as well as single diastereomers of the compounds of the invention are included in the present invention. The terms "S" and "R" configuration, as used herein, are as defined by the IUPAC 1974 "RECOMMENDATIONS FOR SECTION E, FUNDAMENTAL STEREOCHEMISTRY," Pure Appl. Chem. 45:13-30, 1976. The terms α and β are employed for ring positions of cyclic compounds. The α-side of the reference plane is that side on which the preferred substituent lies at the lower numbered position. Those substituents lying on the opposite side of the reference plane are assigned β descriptor. It should be noted that this usage differs from that for cyclic stereoparents, in which "a" means "below the plane" and denotes absolute configuration. The terms α and β configuration, as used herein, are as defined by the "Chemical Abstracts Index Guide," Appendix IV, paragraph 203, 1987.

As used herein, the term "pharmaceutically acceptable salts" refers to the nontoxic acid or alkaline earth metal salts of the compounds of the invention. These salts can be prepared in situ during the final isolation and purification of the compounds, or by separately reacting the base or acid functions with a suitable organic or inorganic acid or base, respectively. Representative salts include, but are not limited to, the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemi-sulfate, heptanoate, hexanoate, fumarate, hydrochloride, hydrobromide, hydroiodide, 2-hydroxyethanesulfonate, lactate, maleate, methanesulfonate, nicotinate, 2-napth-alenesulfonate, oxalate, pamoate, pectinate, persulfate, 3-phenylproionate, picrate, pivalate, propionate, succinate, sulfate, tartrate, thiocyanate, p-toluenesulfonate, and undecanoate. Also, the basic nitrogen-containing groups can be quaternized with such agents as alkyl halides, such as methyl, ethyl, propyl, and butyl chloride, bromides, and iodides; dialkyl sulfates like dimethyl, diethyl, dibutyl, and diamyl sulfates, long chain halides such as decyl, lauryl, myristyl, and stearyl chlorides, bromides and iodides, aralkyl halides like benzyl and phenethyl bromides, and others. Water or oil-soluble or dispersible products are thereby obtained.

Examples of acids that may be employed to form pharmaceutically acceptable acid addition salts include such inorganic acids as hydrochloric acid, sulfuric acid and phosphoric acid and such organic acids as oxalic acid, maleic acid, methanesulfonic acid, succinic acid and citric acid. Basic addition salts can be prepared in situ during the final isolation and purification of the inventive compounds, or separately by reacting carboxylic acid moieties with a suitable base such as the hydroxide, carbonate or bicarbonate of a pharmaceutically acceptable metal cation or with ammonia, or an organic primary, secondary or tertiary amine. Pharmaceutically acceptable salts include, but are not limited to, cations based on the alkali and alkaline earth metals, such as sodium, lithium, potassium, calcium, magnesium, aluminum salts and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like. Other representative organic amines useful for the formation of base addition salts include diethylamine, ethylenediamine, ethanolamine, diethanolamine, piperazine, and the like.

The term "pharmaceutically acceptable prodrugs" as used herein refers to those prodrugs of the compounds of the present invention which are, within the scope of sound medical judgment, suitable for use in contact with the tissues of humans and lower animals without undue toxicity, irritation, allergic response, and the like, commensurate with a reasonable benefit/risk ratio, and effective for their intended use, as well as the zwitterionic forms, where possible, of the compounds of the invention. The term "prodrug" refers to compounds that are rapidly transformed in vivo to yield the parent compound of the above formula, for example by hydrolysis in blood. A thorough discussion is provided in Higuchi, T., and V. Stella, "Pro-drugs as Novel Delivery Systems," A.C.S. Symposium Series 14, and in "Bioreversible Carriers in Drug Design," in Edward B. Roche (ed.), American Pharmaceutical Association, Pergamon Press, 1987, both of which are incorporated herein by reference.

The compounds of the invention are useful in vitro or in vivo in inhibiting the growth of cancer cells. The compounds may be used alone or in compositions together with a pharmaceutically acceptable carrier or excipient. Suitable pharmaceutically acceptable carriers or excipients include, for example, processing agents and drug delivery modifiers and enhancers, such as, for example, calcium phosphate, magnesium stearate, talc, monosaccharides, disaccharides, starch, gelatin, cellulose, methyl cellulose, sodium carboxymethyl cellulose, dextrose, hydroxypropyl-β-cyclodextrin, polyvinyl-pyrrolidinone, low melting waxes, ion exchange resins, and the like, as well as combinations of any two or more thereof. Other suitable pharmaceutically acceptable excipients are described in "Remington's Pharmaceutical Sciences," Mack Pub. Co., New Jersey, 1991, incorporated herein by reference.

Effective amounts of the compounds of the invention generally include any amount sufficient to detectably inhibit MUC1 positive activity by any of the assays described herein, by other MUC1 positive activity assays known to those having ordinary skill in the art, or by detecting an inhibition or alleviation of symptoms of cancer.

The amount of active ingredient that may be combined with the carrier materials to produce a single dosage form will vary depending upon the host treated and the particular mode of administration. It will be understood, however, that the specific dose level for any particular patient will depend upon a variety of factors including the activity of the specific compound employed, the age, body weight, general health, sex, diet, time of administration, route of administration, rate of excretion, drug combination, and the severity of the particular disease undergoing therapy. The therapeutically effective amount for a given situation can be readily determined by routine experimentation and is within the skill and judgment of the ordinary clinician.

For purposes of the present invention, a therapeutically effective dose will generally be a total daily dose administered to a host in single or divided doses may be in amounts, for example, of from 0.001 to 1000 mg/kg body weight daily and more preferred from 1.0 to 30 mg/kg body weight daily. Dosage unit compositions may contain such amounts of submultiples thereof to make up the daily dose.

The compounds of the present invention may be administered orally, parenterally, sublingually, by aerosolization or inhalation spray, rectally, or topically in dosage unit formulations containing conventional nontoxic pharmaceutically acceptable carriers, adjuvants, and vehicles as desired. Topical administration may also involve the use of transdermal administration such as transdermal patches or ionophoresis devices. The term parenteral as used herein includes subcutaneous injections, intravenous, intramuscular, intrasternal injection, or infusion techniques.

Injectable preparations, for example, sterile injectable aqueous or oleaginous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-propanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or di-glycerides. In addition, fatty acids such as oleic acid find use in the preparation of injectables.

Suppositories for rectal administration of the drug can be prepared by mixing the drug with a suitable nonirritating excipient such as cocoa butter and polyethylene glycols, which are solid at ordinary temperatures but liquid at the rectal temperature and will therefore melt in the rectum and release the drug.

Solid dosage forms for oral administration may include capsules, tablets, pills, powders, and granules. In such solid dosage forms, the active compound may be admixed with at least one inert diluent such as sucrose lactose or starch. Such dosage forms may also comprise, as is normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, cyclodextrins, and sweetening, flavoring, and perfuming agents.

The compounds of the present invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients, and the like. The preferred lipids are the phospholipids and phosphatidyl cholines (lecithins), both natural and synthetic. Methods to form liposomes are known in the art. See, for example, Prescott (ed.), "Methods in Cell Biology," Volume XIV, Academic Press, New York, 1976, p. 33 et seq.

While the compounds of the invention can be administered as the sole active pharmaceutical agent, they can also be used in combination with one or more other agents used in the treatment of cancer. Representative agents useful in combination with the compounds of the invention for the treatment of cancer include, for example, irinotecan, topotecan, gemcitabine, gleevec, herceptin, 5-fluorouracil, leucovorin, carboplatin, cisplatin, taxanes, tezacitabine, cyclophosphamide, vinca alkaloids, imatinib, anthracyclines, rituximab, trastuzumab, topoisomerase I inhibitors, as well as other cancer chemotherapeutic agents.

The above compounds to be employed in combination with the compounds of the invention will be used in therapeutic amounts as indicated in the Physicians' Desk Reference (PDR) 47th Edition (1993), which is incorporated herein by reference, or such therapeutically useful amounts as would be known to one of ordinary skill in the art.

The compounds of the invention and the other anticancer agents can be administered at the recommended maximum clinical dosage or at lower doses. Dosage levels of the active compounds in the compositions of the invention may be varied so as to obtain a desired therapeutic response depending on the route of administration, severity of the disease and the response of the patient. The combination can be administered as separate compositions or as a single dosage form containing both agents. When administered as a combination, the therapeutic agents can be formulated as separate compositions, which are given at the same time or different times, or the therapeutic agents, can be given as a single composition.

In hematological cancers, such as chronic myelogenous leukemia (CML), chromosomal translocation is responsible for the constitutively activated BCR-ABL tyrosine kinase. The afflicted patients are responsive to GLEEVEC®, a small molecule tyrosine kinase inhibitor, as a result of inhibition of Abl kinase activity. However, many patients with advanced stage disease respond to GLEEVEC® initially, but then relapse later due to resistance-conferring mutations in the Ab1 kinase domain. In vitro studies have demonstrated that BCR-Av1 employs the Raf kinase pathway to elicit its effects. In addition, inhibiting more than one kinase in the same pathway provides additional protection against resistance-conferring mutations. Accordingly, in another aspect of the invention, the inventive compounds are used in combination with at least one additional agent, such as GLEEVEC®, in the treatment of hematological cancers, such as chronic myelogenous leukemia (CML), to reverse or prevent resistance to the at least one additional agent.

In another aspect of the invention, kits that include one or more compounds of the invention are provided. Representative kits include a compound of the invention and a package insert or other labeling including directions for treating a cellular proliferative disease by administering MUC1* inhibitory amount of the compound.

Structure of Compounds

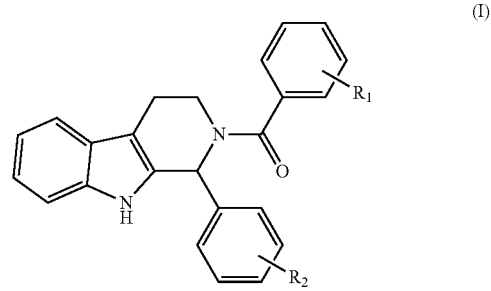

(I)

or a steroisomer, tautomer, pharmaceutically acceptable salt, ester, or prodrug thereof, wherein, the ring to which R1 connects is optionally substituted with between 0 and 5 substituents independently selected from halogen, haloalkane, lower alkyl, branched lower alkyl, cyclic alkyl, —OH, alkylene, alkylether such as —OCH$_3$, —NH$_2$, mono- or di-substituted amine, cycloalkylamine, —NO$_2$, —CN, —NHCOCH$_3$, —NHCO-alkyl, and —NHSO$_2$CH$_3$.

The halogen may be selected from the group consisting of F, Cl, Br and I. Preferably, the halogen is Cl or F.

The haloalkane may be selected from the group consisting of CF$_3$ and C$_2$F$_5$, Preferably, the haloalkane is CF$_3$.

The lower alkyl may be selected from the group consisting of methyl, ethyl and propyl. Preferably, the lower alkyl is methyl.

The mono- or di-substituted amine may be selected from the group consisting of alkylsubstituted amine, such as but not limited to —NHCH$_3$ and —N(CH$_3$)$_2$, or cycloalkylamine, such as but not limited to piperidine, piperazine, morpholine, pyrrolidine.

The alkylene may be without limitation —CH=CH—CH=CH—.

The alkylether may be without limitation —OMe.

the ring to which R2 connects is optionally substituted with 0 to 5 substituents independently selected from halogen, haloalkane, lower alkyl, branched alkyl, —OH, —NH$_2$, mono- or di-substituted amine, cyclic amine, alkylether, and H.

The halogen may be selected from the group consisting of F, Cl, Br and I. Preferably, the halogen is Cl.

The haloalkane may be selected from the group consisting of CF$_3$ and C$_2$F$_5$, Preferably, the haloalkane is CF$_3$.

The lower alkyl may be selected from the group consisting of methyl, ethyl and propyl. Preferably, the lower alkyl is methyl.

The mono- or di-substituted amine may be selected from the group consisting of alkylsubstituted amine, such as but not limited to —NHCH$_3$ and —N(CH$_3$)$_2$, or cycloalkylamine, such as but not limited to piperidine, piperazine, morpholine, pyrrolidine.

The alkylether may be without limitation —OMe.

Optionally, the ring to which R1 connects is optionally substituted with between 0 and 5 substituents independently selected from F, Cl, CF$_3$, Me, —N(CH$_3$)$_2$, —OH, alkylene, alkylether such as —OCH$_3$, —NO$_2$, and —CN; and the ring to which R2 connects is optionally substituted with 0 to 5 substituents independently selected from —Cl, —OMe, CF$_3$ and H.

Optionally, the substituents may be selected from the following:
R1 may be selected from the group consisting of
2-, 3-, or 4-Cl,
any combination of di-chloro substitution, including but not limited to 3,5-di-Cl,
2-, 3-, or 4-Me,
any combination of dimethyl including but not limited to 2,3-di-Me,
2-, 3-, or 4-CF$_3$,
2-, 3-, 4-F,
2,3,4,5,6-per-F,
CH═CH—CH═CH—
OCH$_3$,
4-N(CH$_3$)$_2$,
4-NO$_2$, and
4-CN; and
R2 may be selected from the group consisting of
4-Cl,
4-OMe,
4-CF$_3$, and
H.

Optionally, the substituents may be selected from the following:
R1 may be selected from the group consisting of
3- or 4-Cl
3- or 4-Me,
2,3-di-Me,
3,5-di-Cl,
3- or 4-CF$_3$,
2,3,4,5,6-per-F,
OCH$_3$,
4-N(CH$_3$)$_2$,
4-NO$_2$, and
4-CN; and
R2 may be selected from the group consisting of
4-Cl,
4-OMe,
4-CF$_3$, and
H.

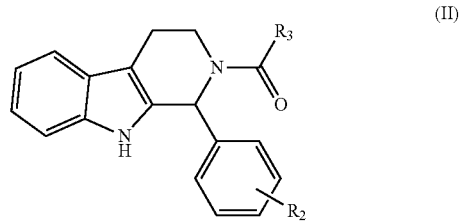

(II)

or a stereoisomer, tautomer, pharmaceutically acceptable salt, ester, or prodrug thereof, wherein,
R2 is same as above.
R3 is selected from the group consisting of alkyl, —CH$_2$—O-cycloaryl, —CH$_2$—O-aryl, —CH$_2$NHCO-cycloalkyl, CH$_2$NHCO-alkyl cycloalkyl, 2-propyl, branched alkyl, thiofuranyl, aryl, heteroaryl, naphthyl, or phenyl optionally substituted with between 0 and 5 substituents independently selected from halogen, haloalkanes, lower alkyl, branched lower alkyl, cyclic alkyl, —NH$_2$, mono- or di-substituted amines, cycloalkylamines, —NO$_2$, —CN, —NHCOCH$_3$, —NHCO-alkyl and —NHSO$_2$CH$_3$.

The halogen may be selected from the group consisting of F, Cl, Br and I. Preferably, the halogen is Cl or F.

The haloalkane may be selected from the group consisting of CF$_3$ and C2F$_5$, Preferably, the haloalkane is CF$_3$.

The lower alkyl may be selected from the group consisting of methyl, ethyl propyl, and 2-propyl. Preferably, the lower alkyl is methyl or 2-propyl.

The mono- or di-substituted amine may be selected from the group consisting of alkylsubstituted amine, such as but not limited to —NHCH$_3$ and —N(CH$_3$)$_2$, or cycloalkylamine, such as but not limited to piperidine, piperazine, morpholine, pyrrolidine.

The alkylether may be without limitation —OMe.

Optionally, the ring to which R2 connects is optionally substituted with 0 to 5 substituents independently selected from —Cl, —OMe, CF$_3$ and H; and R3 substituent is selected from alkyl, —CH$_2$—O-cycloaryl, —CH$_2$—O-aryl, —CH$_2$NHCO-cycloalkyl, CH$_2$NHCO-alkyl cycloalkyl, 2-propyl, branched alkyl, thiofuranyl, heteroaryl, or phenyl optionally substituted with between 0 and 5 substituents independently selected from F, Cl, CF$_3$, Me, —N(CH$_3$)$_2$, —NO$_2$, or —CN.

Optionally, the substituents may be selected from the following:
R2 may be selected from the group consisting of
4-Cl;
4-OMe,
4-CF$_3$, and
H.
R3 may be alkyl, cycloalkyl, 2-propyl, branched alkyl, thiofuranyl, aryl, heteroaryl, naphthyl, or phenyl optionally substituted with one or more of the following substituents:
2-, 3-, or 4-Cl,
CH$_2$NHCO—C$_5$H$_9$,
CH$_2$O—C$_6$H$_5$,
any combination of di-chloro substitution, including but not limited to 3,5-di-Cl,
2-, 3-, or 4-Me,
any combination of dimethyl including but not limited to 2,3-di-Me,
2-, 3-, or 4-CF$_3$,
2-, 3-, or 4-F,
2, 3, 4,5,6-per-F,
4-N(CH$_3$)$_2$,
4-NO$_2$, or
4-CN.

Optionally, the substituents may be selected from the following:
R2 may be selected from the group consisting of
4-Cl;
4-OMe,
4-CF$_3$, and
H.
R3 may be cyclopentyl, 2-thiofuranyl, naphthyl, or phenyl optionally substituted with one or more of the following substituents:
3-, or 4-Cl,
4-F,
2,3,4,5,6-per-fluoro,
2,4-di-Cl,
3,5-di-Cl,
3,4-di-Cl,
4-OCH$_3$,
CH$_2$NHCO—C$_5$H$_9$,
CH$_2$O—C$_6$H$_5$,
3-, or 4-CF$_3$,
4-CN,
2-, 3-, or 4-Me,
2,3-di-Me,
4-t-Bu,
4-NO$_2$,
4-N(CH$_3$)$_2$, or
H.

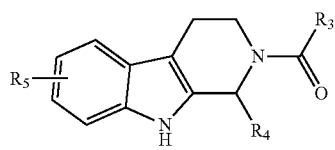
(III)

or a steroisomer, tautomer, pharmaceutically acceptable salt, ester, or prodrug thereof, wherein,
R$_3$ is described above;
R4 is selected from alkyl, branched alkyl, cycloalkyl, heteroaryl, or any ring or ring system optionally substituted with 0 to 5 substituents independently selected from halogen, CF$_3$, lower alkyl, branched alkyl, —OH, —NH$_2$, mono-, or di-substituted amines, including but not limited to cyclic amines such as morpholine, pyrrolidine, piperazine, piperidine, and alkylethers such as but not limited to —OMe, and H; and
R5 is selected from halogen, lower alkyl, haloalkyl, alkylether such as but not limited to —OMe, —NH$_2$, mono-, and di-substituted amines, including but not limited to cyclic amines such as morpholine, pyrrolidine, piperazine, and piperidine, and H.
Optionally, the substituents may be selected from the following:
R3 is selected from alkyl, cycloalkyl, 2-propyl, branched alkyl, thiofuranyl, heteroaryl, or phenyl optionally substituted with between 0 and 5 substituents independently selected from halogen, such as F, Cl, Br, I, haloalkanes, such as CF$_3$, lower alkyl such as methyl, ethyl, propyl, dialkyl-substituted amines such as —N(CH$_3$)$_2$, —NO$_2$, —CN;
R4 is selected from an aromatic ring optionally substituted with 0 to 5 substituents independently selected from halogen, lower alkyl, haloalkyl, alkylether such as —OMe, and H; and
R5 is selected from halogen, lower alkyl, haloalkyl, alkylether such as —OMe, and H.
Optionally, the substituents may be selected from the following:
R3 is selected from alkyl, cycloalkyl, 2-propyl, branched alkyl, thiofuranyl, heteroaryl, or phenyl optionally substituted with between 0 and 5 substituents independently selected from F, Cl, CF$_3$, Me, —N(CH$_3$)$_2$, —NO$_2$, and —CN,
R4 is selected from aromatic ring optionally substituted with 0 to 5 substituents independently selected from halogen, alkyloxy, haloalkyl and H; and
R5 is selected from H, F, Cl, OCH$_3$, CH$_3$, CN, NO$_2$, or NH$_2$.
Optionally, the substituents may be selected from the following:
R3 is selected from alkyl, cycloalkyl, 2-propyl, branched alkyl, thiofuranyl, heteroaryl, or phenyl optionally substituted with one or more of the following substituents:
2-, 3, or 4-Cl,
any combination of di-chloro substitution, including but not limited to 3,5-di-Cl,
2-, 3-, or 4-Me,
any combination of dimethyl including but not limited to 2,3-di-Me,
2-, 3-, or 4-CF$_3$,
2-, 3-, or 4-F,
2,3,4,5,6-per-F,
4-N(CH$_3$)$_2$,
4-NO$_2$,
4-CN;
R4 is selected from phenyl ring optionally substituted with Cl, OMe, and H, CF$_3$; and
R5 is selected from H, F, and Cl.
Optionally, the substituents may be selected from the following:
R3 is selected from cyclopentyl, 2-thiofuranyl, and phenyl optionally substituted with one or more of the following substituents:
H,
3-, or 4-Cl,
4-F,
2,3,4,5,6-per-fluoro,
2,4-di-Cl,
3,5-di-Cl,
3,4-di-Cl,
4-OCH$_3$,
3-, or 4-CF$_3$,
4-CN,
2-, 3-, or 4-Me,
2,3-di-Me,
4-t-Bu,
4-NO$_2$,
4-N(CH$_3$)$_2$;
R4 is a phenyl ring optionally substituted with H, 4-OCH$_3$, 4-Cl, or 4-CF$_3$; and
R5 is H.

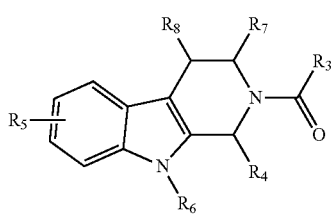
(IV)

or a steroisomer, tautomer, pharmaceutically acceptable salt, ester, or prodrug thereof, wherein,
R3 is described above;
R4 is described above;
R5 is described above;
R6 is H or alkyl;

R7 is H or alkyl, —OH, —NH₂, mono-, and di-substituted amines, including cyclic amines such as morpholine, pyrrolidine, piperazine, and piperidine; and R8 is H or alkyl.

Optionally, the substituents may be selected from the following:

R3 is selected from alkyl, cycloalkyl, 2-propyl, branched alkyl, thiofuranyl, heteroaryl, or phenyl optionally substituted with between 0 and 5 substituents independently selected from halogen, including F, Cl, Br, and I, haloalkanes, such as CF₃, lower alkyl such as methyl, ethyl, propyl, dialkyl-substituted amines such as —N(CH₃)₂, —NO₂, and —CN;

R4 is selected from an aromatic ring optionally substituted with 0 to 5 substituents independently selected from halogen, lower alkyl, haloalkyl, alkylethers such as —OMe, and H;

R5 is selected from halogen, lower alkyl, haloalkyl, alkylether such as —OMe, and H;

R6 is H or alkyl;

R7 is H, alkyl, —OH, or —NH₂; and

R8 is H or alkyl.

Optionally, the substituents may be selected from the following:

R3 is alkyl, cycloalkyl, 2-propyl, branched alkyl, thiofuranyl, heteroaryl, or phenyl optionally substituted with between 0 and 5 substituents independently selected from F, Cl, CF₃, Me, —N(CH₃)₂, —NO₂, and —CN;

R4 is aromatic ring optionally substituted with 0 to 5 substituents independently selected from halogen, alkyloxy, haloalkyl and H;

R5 is H, F, Cl, OCH₃, CH₃, CN, NO₂, or NH₂;

R6 is H or alkyl;

R7 is H or alkyl; and

R8 is H or alkyl.

Optionally, the substituents may be selected from the following:

R3 is selected from alkyl, cycloalkyl, 2-propyl, branched alkyl, thiofuranyl, heteroaryl, or phenyl optionally substituted with one or more of the following substituents: 2-, 3-, or 4-Cl, any combination of di-chloro substitution, including but not limited to 3,5-di-Cl,
2-, 3-, or 4-Me,
any combination of dimethyl including but not limited to 2,3-di-Me,
2-, 3-, or 4-CF₃,
2-, 3-, 4-F,
2,3,4,5,6-per-F,
4-N(CH₃)₂,
4-NO₂, and
4-CN;

R4 is phenyl ring optionally substituted with Cl, OMe, H, or CF₃;

R5 is H, F, or Cl;

R6 is H or CH₃;

R7 is H or CH₃; and

R8 is H or CH₃.

Optionally, the substituents may be selected from the following:

R3 is selected from cyclopentyl, 2-thiofuranyl, phenyl optionally substituted with one or more of the following substituents:
H,
3-, 4-Cl,
4-F,
2,3,4,5,6-per-fluoro,
2,4-di-Cl,
3,5-di-Cl,
3,4-di-Cl,
4-OCH₃,
3-, 4-CF₃,
4-CN,
2-, 3-, 4-Me,
2,3-di-Me,
4-t-Bu,
4-NO₂, and
4-N(CH₃)₂;

R4 is phenyl ring optionally substituted with H, 4-OCH₃, 4-Cl, or 4-CF₃;

R5 is H;

R6 is H;

R7 is H; and

R8 is H.

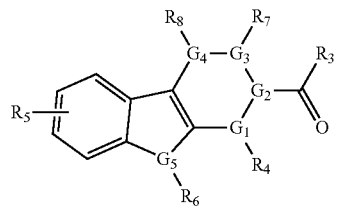

(V)

or a stereoisomer, tautomer, pharmaceutically acceptable salt, ester, or prodrug thereof, wherein, R3 is described above;
R4 is described above;
R5 is described above;
R6 is described above;
R7 is described above;
R8 is described above;
G1 is CH;
G2 is N;
G3 is CH, CH₂, NH;
G4 is CH or CH₂; and
G5 is N, O, or S.

Optionally, the substituents may be selected from the following:

R3 is selected from alkyl, cycloalkyl, 2-propyl, branched alkyl, thiofuranyl, heteroaryl, or phenyl optionally substituted with between 0 and 5 substituents independently selected from halogen, such as F, Cl, Br, I, haloalkane, such as CF₃, lower alkyl such as methyl, ethyl, propyl, dialkyl-substituted amines such as —N(CH₃)₂, —NO₂, and —CN;

R4 is selected from an aromatic ring optionally substituted with 0 to 5 substituents independently selected from halogen, lower alkyl, haloalkyl, alkylether such as —OMe, and H;

R5 is selected from halogen, lower alkyl, haloalkyl, alkylethers such as —OMe, and H;

R6 is H or alkyl;

R7 is H or alkyl, —OH, or —NH₂;

R8 is H or alkyl;

G1 is CH;

G2 is N;

G3 is CH, CH₂, or NH;

G4 is CH or CH₂; and

G5 is N, O, or S.

Optionally, the substituents may be selected from the following:

R3 is selected from alkyl, cycloalkyl, 2-propyl, branched alkyl, thiofuranyl, heteroaryl, or phenyl optionally substituted with between 0 and 5 substituents independently selected from: F, Cl, $CF_3$, Me, $-N(CH_3)_2$, $-NO_2$, and $-CN$;

R4 is aromatic ring optionally substituted with 0 to 5 substituents independently selected from halogen, alkyloxy, haloalkyl and H;

R5 is H, F, Cl, $OCH_3$, $CH_3$, CN, $NO_2$, or $NH_2$;
R6 is H or alkyl;
R7 is H or alkyl;
R8 is H or alkyl;
G1 is CH;
G2 is N;
G3 is CH, $CH_2$, or NH;
G4 is CH or $CH_2$; and
G5 is N, O or S.

Optionally, the substituents may be selected from the following:

R3 is selected from alkyl, cycloalkyl, 2-propyl, branched alkyl, thiofuranyl, heteroaryl, or phenyl optionally substituted with one or more of the following substituents:
2-, 3-, or 4-Cl,
any combination of di-chloro substitution, including but not limited to 3,5-di-Cl,
2-, 3-, or 4-Me,
any combination of dimethyl including but not limited to 2,3-di-Me,
2-, 3-, or 4-$CF_3$,
2-, 3-, or 4-F,
2,3,4,5,6-per-F,
4-$N(CH_3)_2$,
4-$NO_2$,
4-CN;

R4 is phenyl ring optionally substituted with Cl, OMe, H, or $CF_3$;
R5 is H, F or Cl;
R6 is H or $CH_3$;
R7 is H or $CH_3$;
R8 is H or $CH_3$;
G1 is CH;
G2 is N;
G3 is CH or $CH_2$;
G4 is CH or $CH_2$; and
G5 is N.

Optionally, the substituents may be selected from the following:

R3 is selected from cyclopentyl, 2-thiofuranyl, phenyl optionally substituted with one or more of the following substituents:
H,
3-, or 4-Cl,
4-F,
2, 3,4,5,6-per-fluoro,
2,4-di-Cl,
3,5-di-Cl,
3,4-di-Cl,
4-$OCH_3$,
3-, or 4-$CF_3$,
4-CN,
2-, 3-, 4-Me,
2,3-di-Me,
4-t-Bu,
4-$NO_2$,
4-$N(CH_3)_2$;

R4 is phenyl ring optionally substituted with H, 4-$OCH_3$, 4-Cl, 4-$CF_3$;
R5 is H;
R6 is H;
R7 is H;
R8 is H;
G1 is CH;
G2 is N;
G3 is CH or $CH_2$;
G4 is CH or $CH_2$; and
G5 is N.

Activities of Compounds Having Specific Activity Against Cancer Cells

Chemotype 4 Compounds.

Two parent compounds:

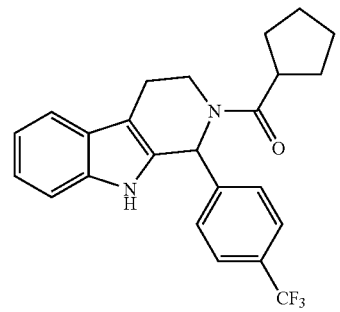

128A3

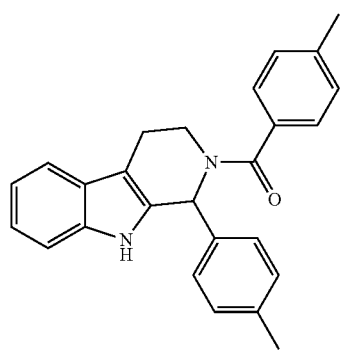

132C9

All analog compounds that were tested include the following:

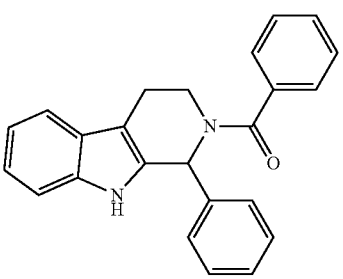

MN341

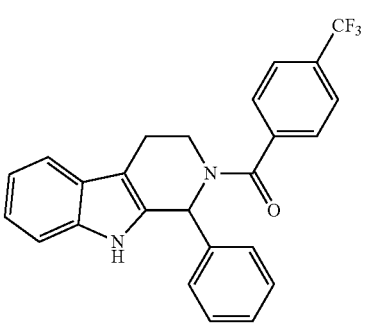

MN342

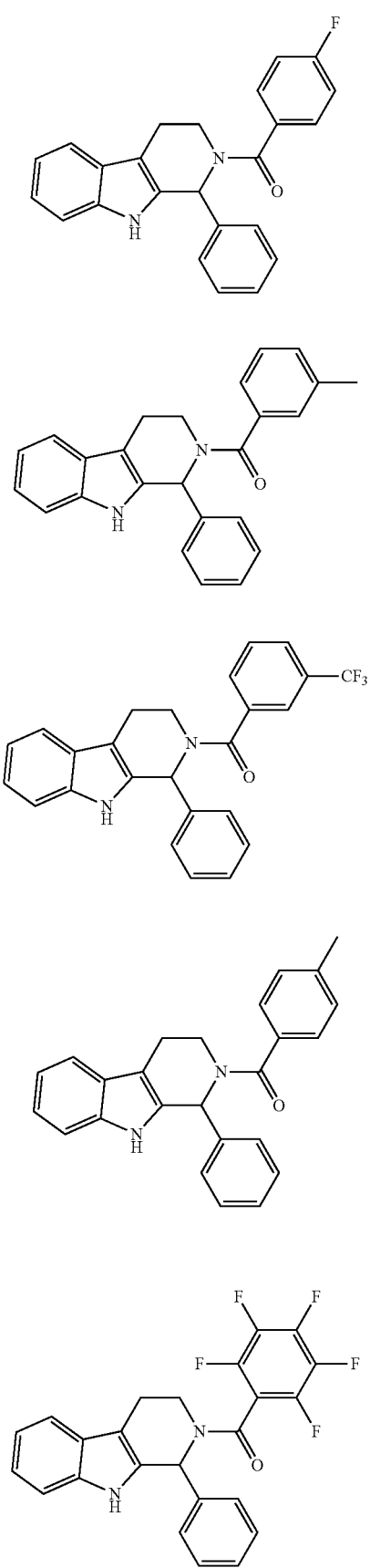
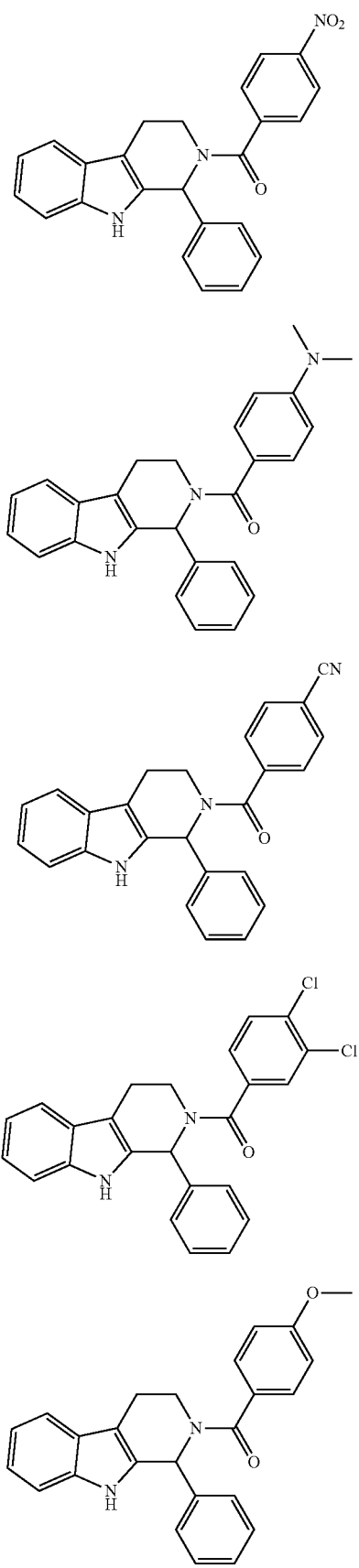

MN353
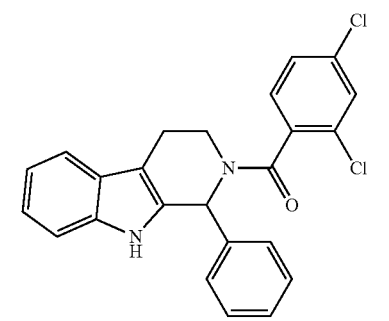
MN354
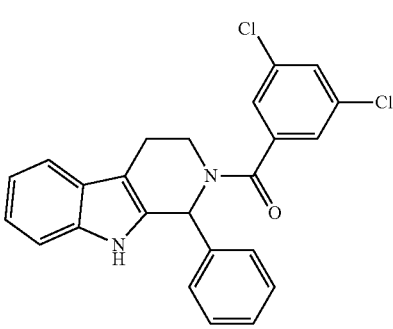
MN355
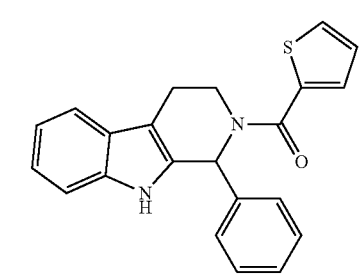
MN356
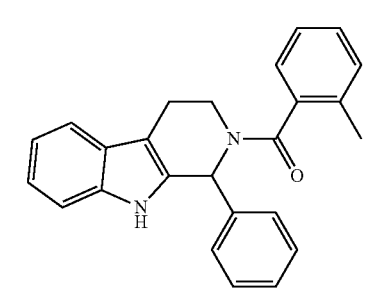
MN357
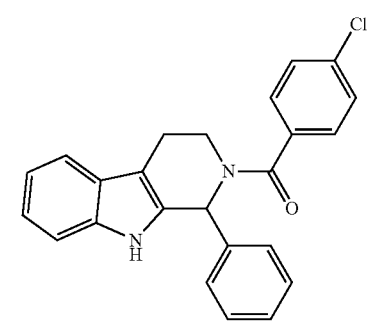
MN358
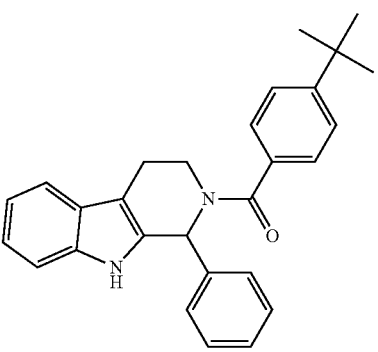
MN359
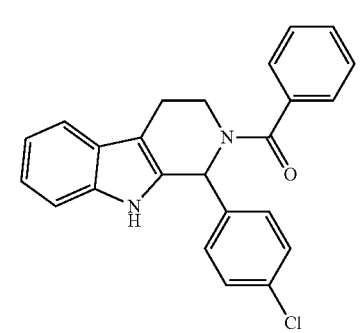
MN360
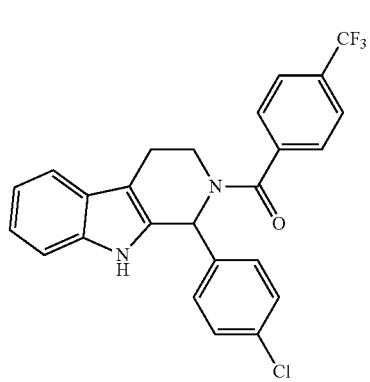
MN361
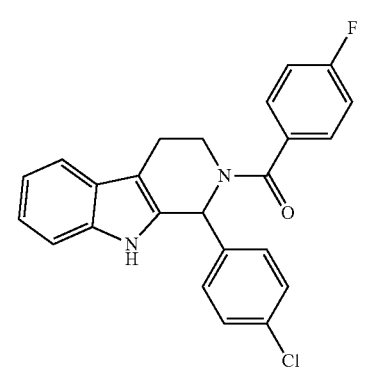

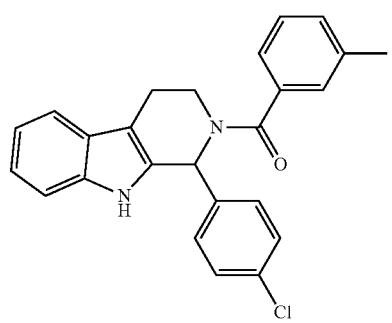
MN362
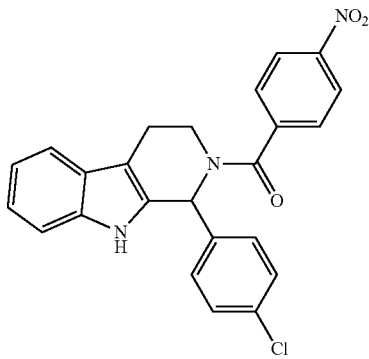
MN366
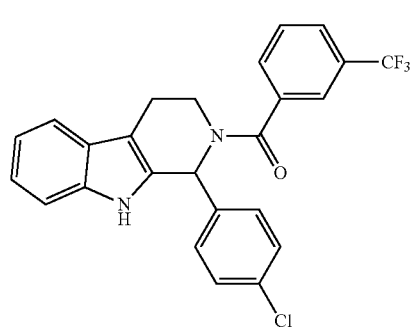
MN363
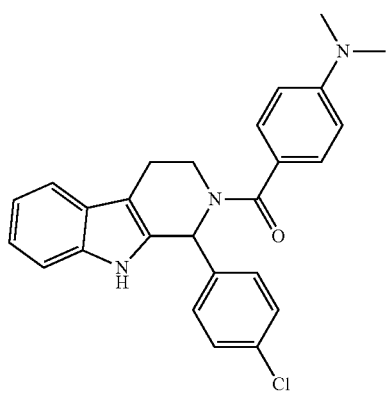
MN367
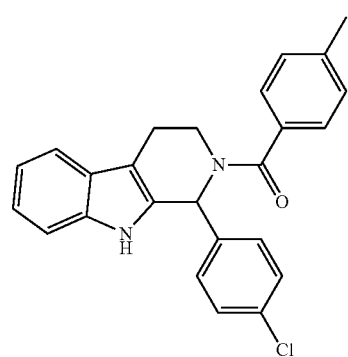
MN364
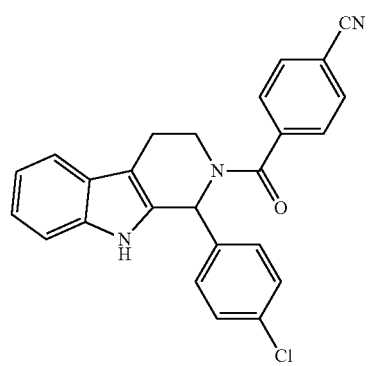
MN368
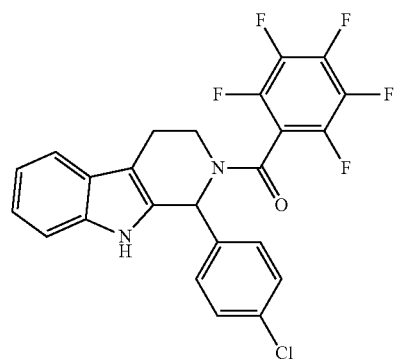
MN365
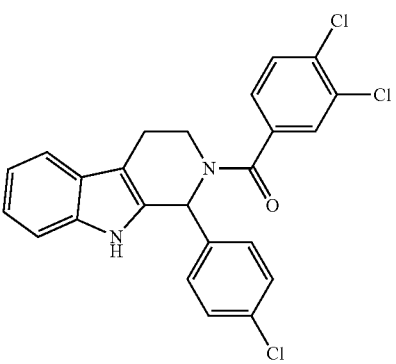
MN369

-continued
MN370
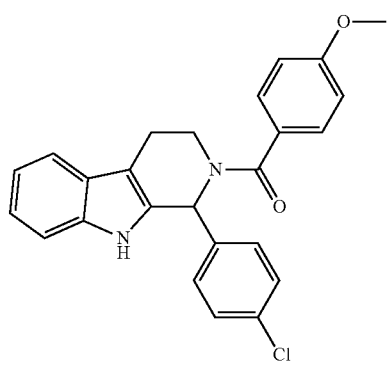
MN371
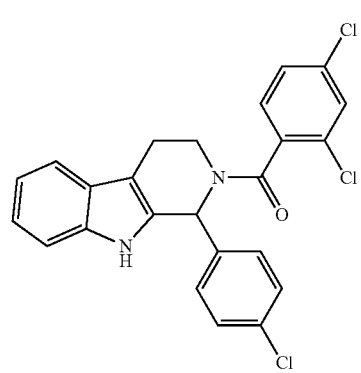
MN372
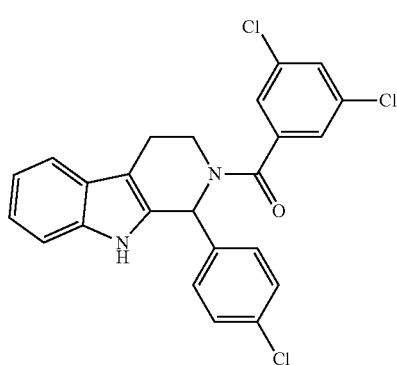
MN373
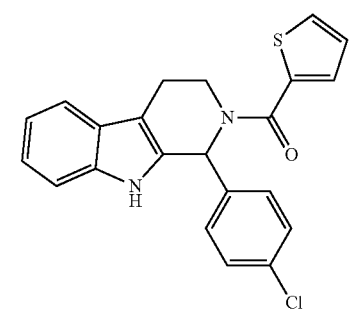
-continued
MN374
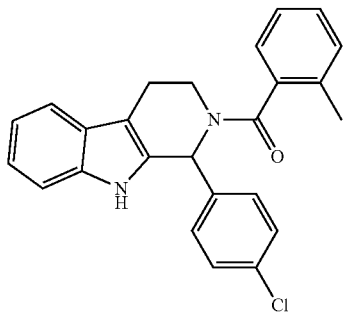
MN375
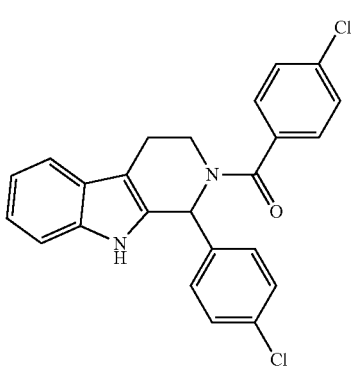
MN376
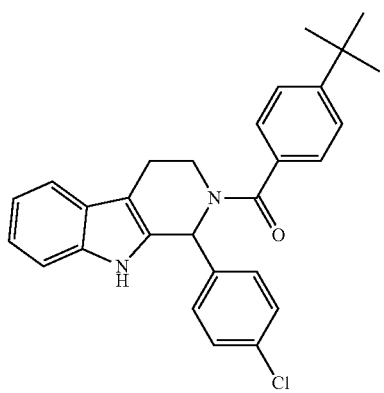
MN377
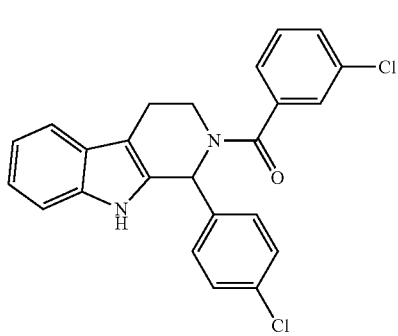

-continued
MN378
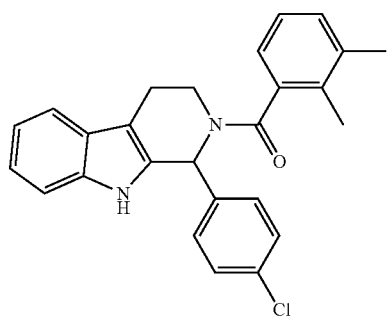
MN379
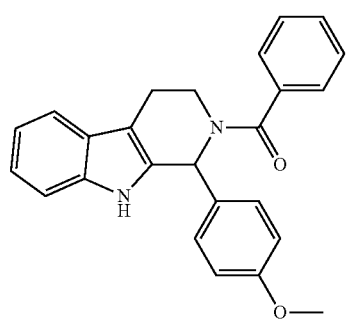
MN380
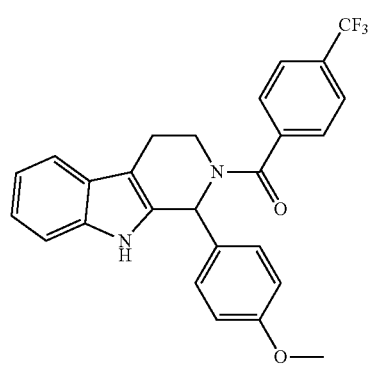
MN381
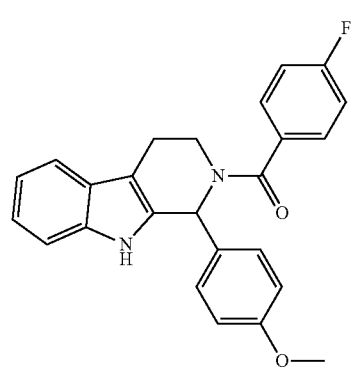
-continued
MN382
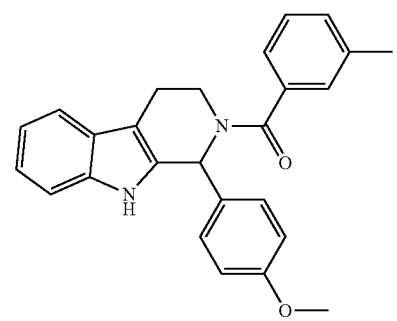
MN383
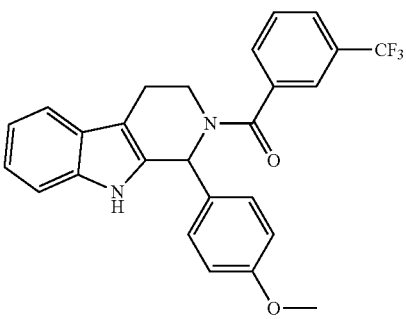
MN384
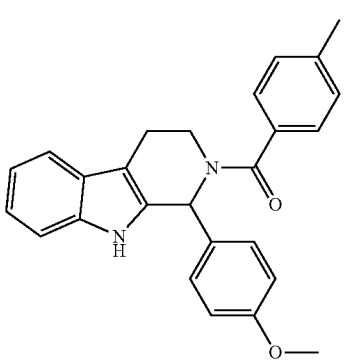
MN385
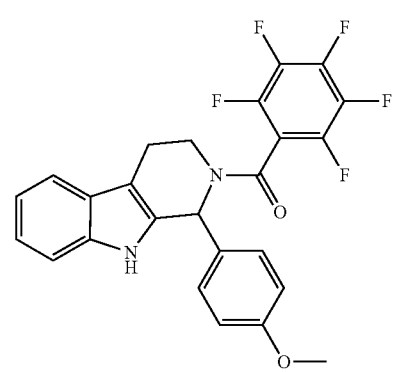

MN386
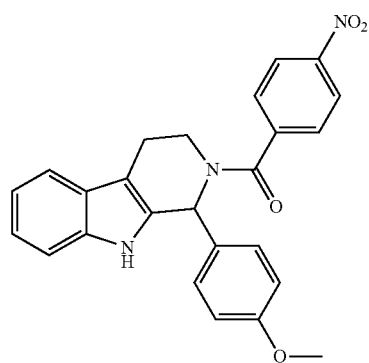
MN387
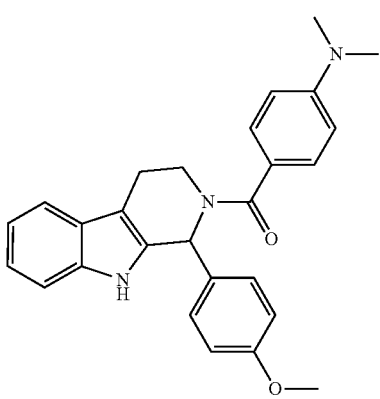
MN388
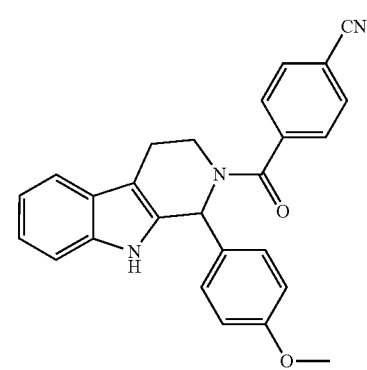
MN389
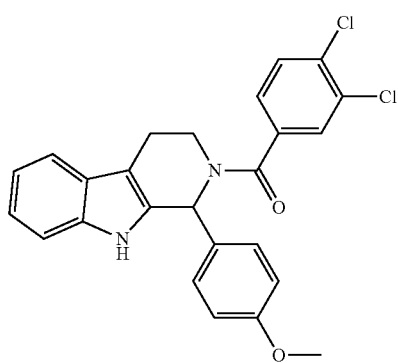
MN390
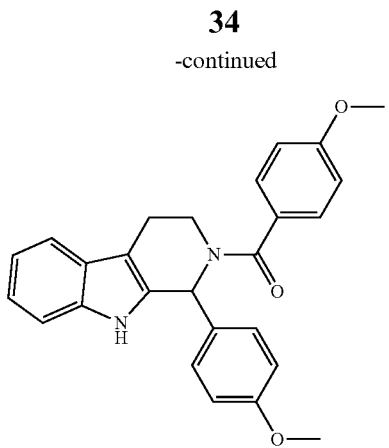
MN391
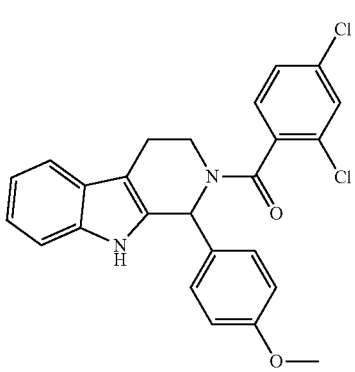
MN392
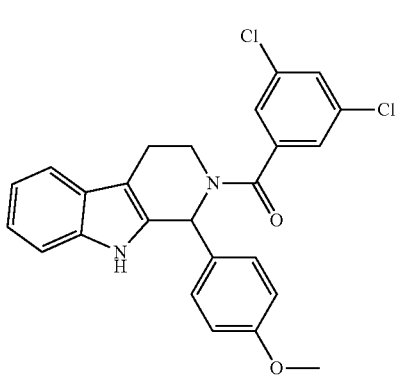
MN393
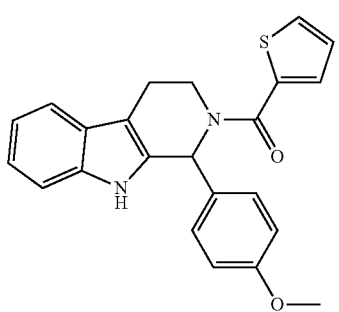

-continued
MN394
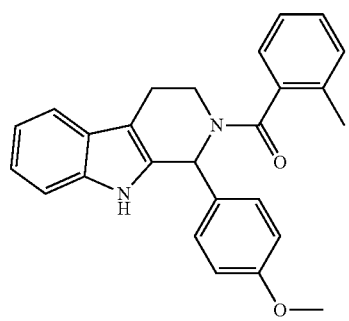
MN398
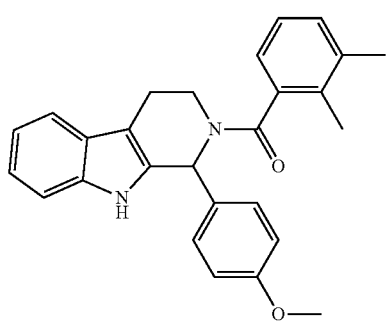
Other analog compounds:
MN395
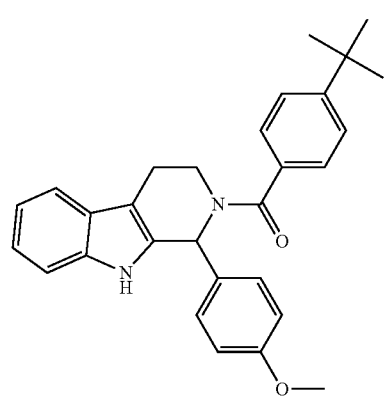
MN300
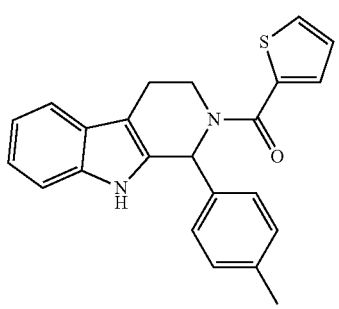
MN396
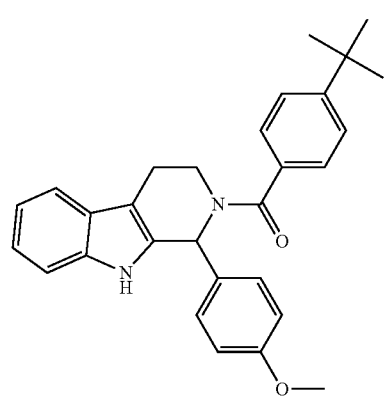
MN301
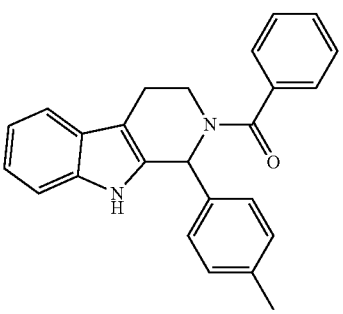
MN397
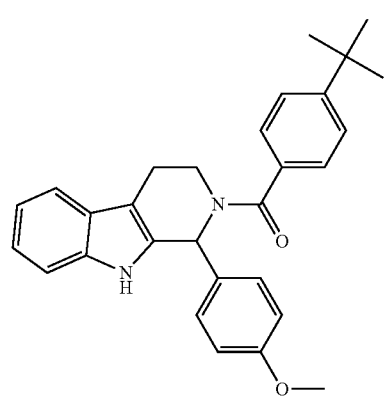
MN302
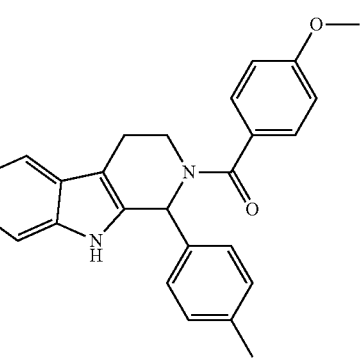

MN303
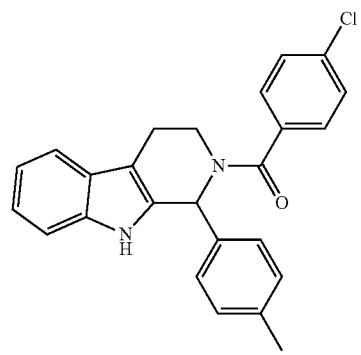
MN304
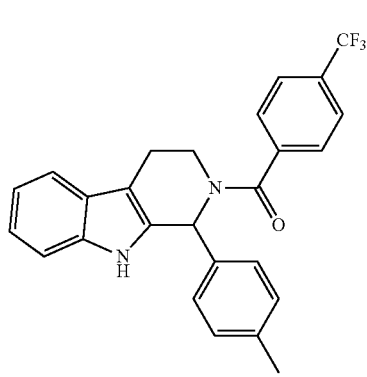
MN325
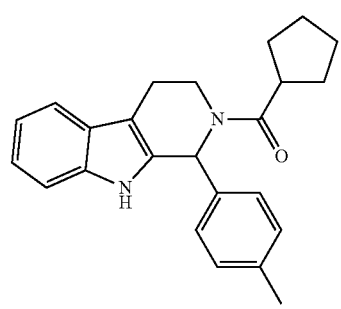
MN326
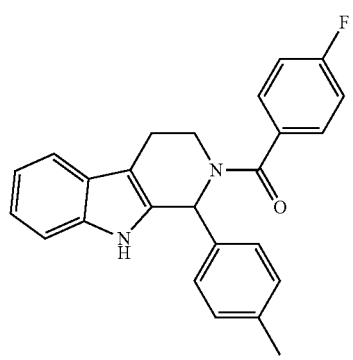
MN327
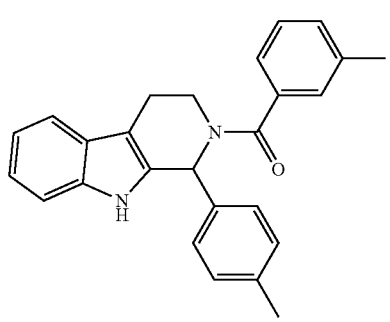
MN328
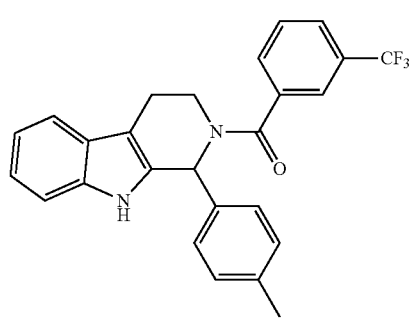
MN329
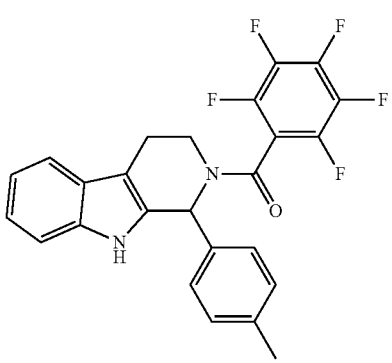
MN330
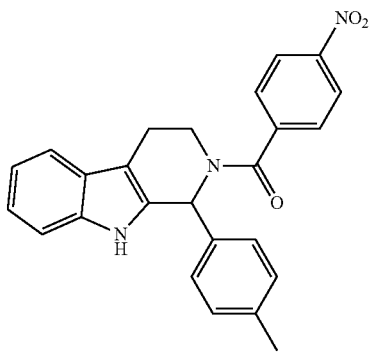

-continued
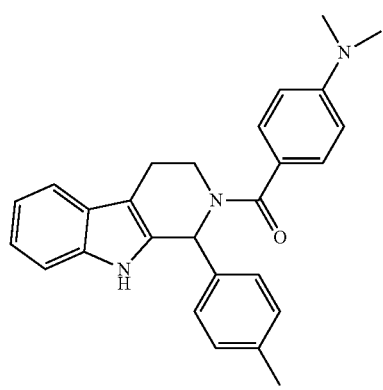
MN331
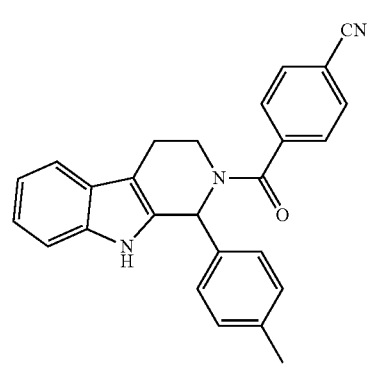
MN332
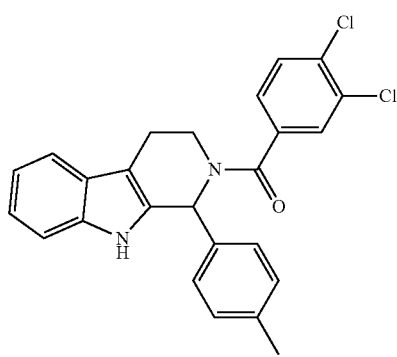
MN333
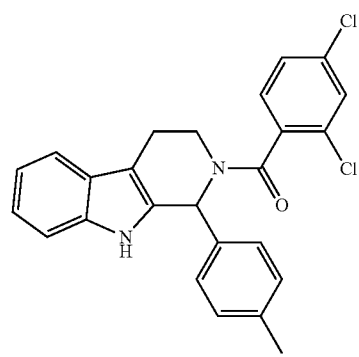
MN335
-continued
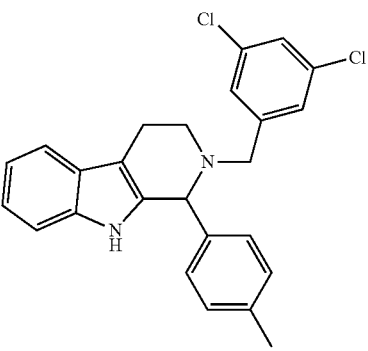
MN336
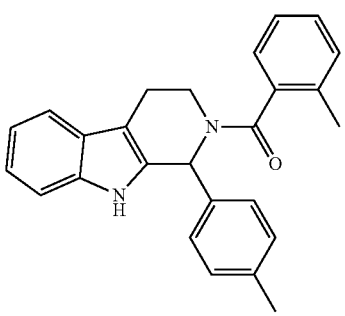
MN338
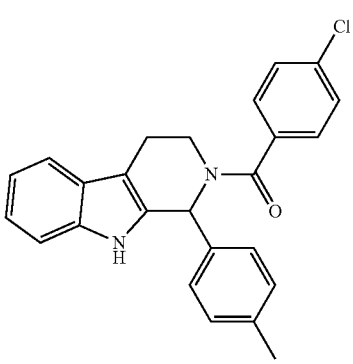
MN339
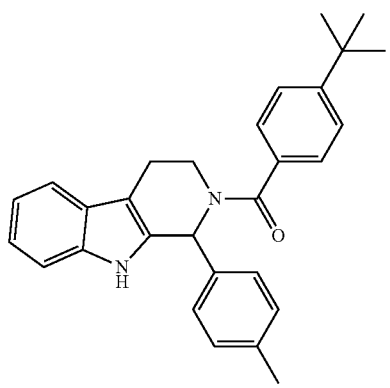
MN340

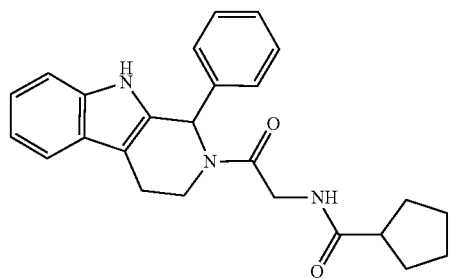
CGX-0536615
132F9
T47D-100; K293 32; [K293-T47D] 132
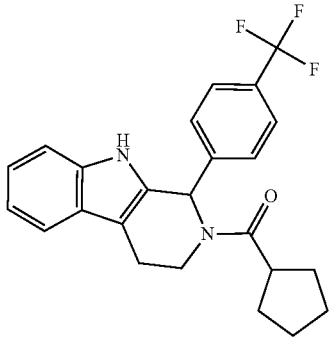
CGX-0500116
128A3
T47D-72; K293 45; [K293-T47D] 117
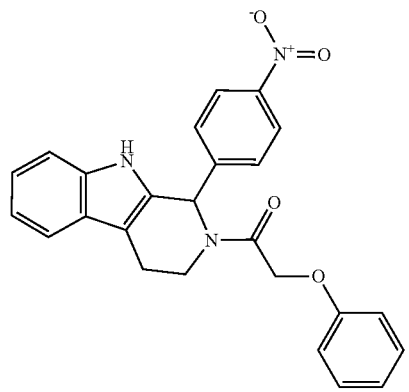
CGX-0499824
63B11
T47D-77; K293 46; [K293-T47D] 123
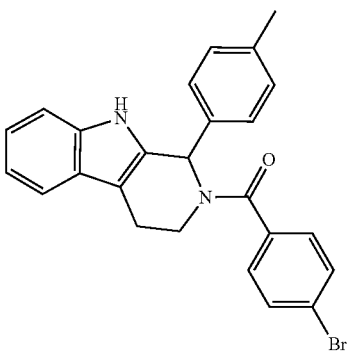
CGX-0523850
130A7
T47D-90; K293 19; [K293-T47D] 109
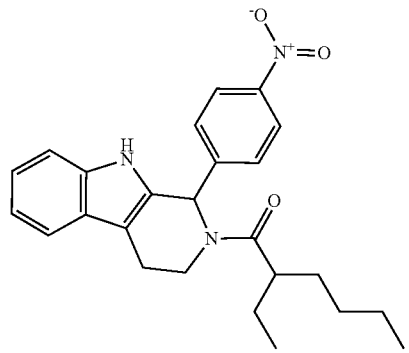
CGX-0499826
58G6
T47D-100; K293 19; [K293-T47D] 119
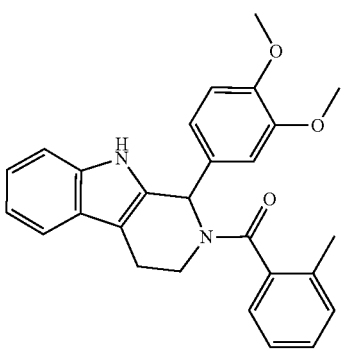
CGX-0494775
64C10
T47D-100; K293-16; [K293-T47D] 84

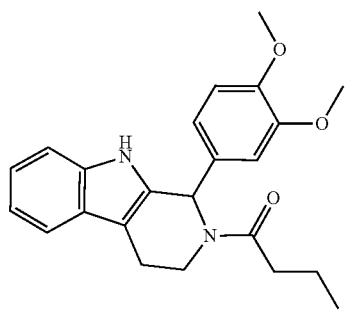

CGX-0494750
64D5
T47D-100; K293-22; [K293-T47D] 78

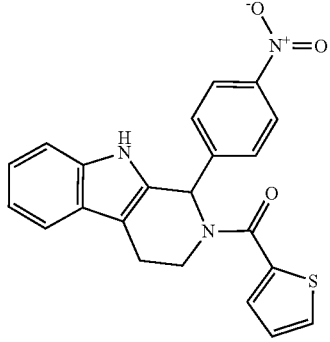

CGX-0499815
36 H6
T47D -2; K293 41; [K293-T47D] 43

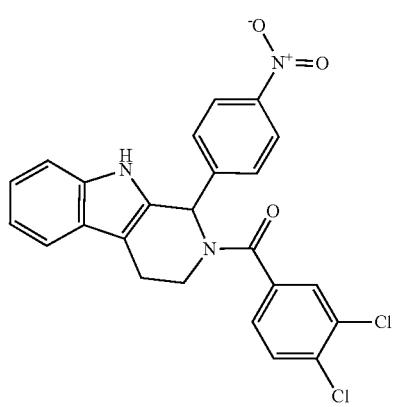

CGX-0499832
20A9
T47D -35; K293 15; [K293-T47D] 50

MN407

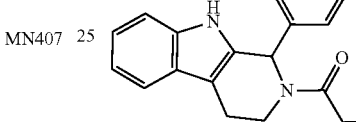

CGX-049729
99F2
T47D 35; K293 35; [K293-T47D] 0

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims. The following examples are offered by way of illustration of the present invention, and not by way of limitation.

MN408

EXAMPLES

Synthesis Schemes for Chemotype 4 Compounds

A. Synthesis scheme for compound 128A3

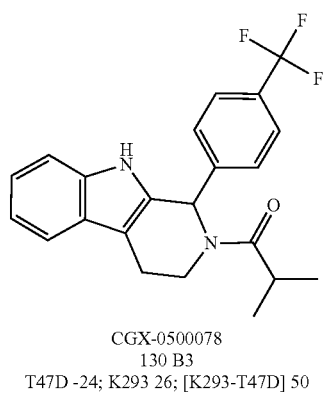

CGX-0500078
130 B3
T47D -24; K293 26; [K293-T47D] 50

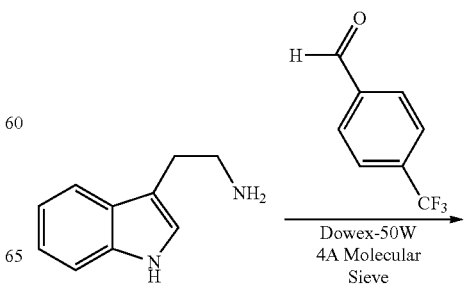

-continued

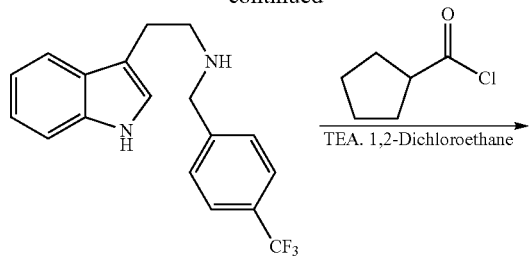

128A3

Example 1

Synthesis of cyclopentyl-[1-(4-trifluoromethyl-phenyl)-1,3,4,9-tetrahydro-β-carbolin-2-yl]-methanone (compound 128A3)

Example 1.1

1-(4-Trifluoromethyl-phenyl)-2,3,4,9-tetrahydro-1H-β-carboline

A dry 500 ml round bottomed flask, equipped with a stir bar was charged with 5.0 g of tryptamine (1 eq.), 2.0 g of Dowex-50W, 5.0 g of 4 Å molecular sieves (as a dehydrating agent) and 150 ml of chloroform. 5.4 g (1 eq.) of 4-(Trifluoromethyl)benzaldehyde was added via syringe, followed by the addition of 1.0 ml of trifluoroacetic acid (0.42 eq.) The reaction mixture was gently stirred. Completion of the reaction was monitored by TLC, after which 1,2-DCE was added to reaction mixture. Solvents were removed to give the crude title product which was used for next step without purification.

Example 1.2

Cyclopentyl-[1-(4-trifluoromethyl-phenyl)-1,3,4,9-tetrahydro-β-carbolin -2-yl]-methanone A dry 500 ml round bottomed flask, equipped with a large stir bar was charged with 31.2 mmol of crude 1-(4-trifluoromethyl-phenyl)-2,3,4,9-tetrahydro-1H-β-carboline (1 eq.), 4.76 g of triethylamine (1.5 eq.) and 300 ml of 1,2-DCE. After the reaction vessel was sealed, 4.14 g (1 eq.) of cyclopentanecarbonyl chloride was added via syringe dropwise. Completion of the reaction was monitored by TLC, after which the solution was quenched with 100 ml of saturated $NaHCO_3$ aqueous solution and diluted with 500 ml of ethyl acetate. The organic layer was separated, washed with brine and dried with $NaSO_4$. After the solvent was removed, flash chromatography (3% $CH_3OH/CH_2Cl_2$ with 0.25% $NH_4OH$) allowed isolation of the title product (1.5 g, 12% for two steps) as a yellow solid.

B. Synthesis Schemes for Compounds MN341-MN358

Compounds with phenyl substitution

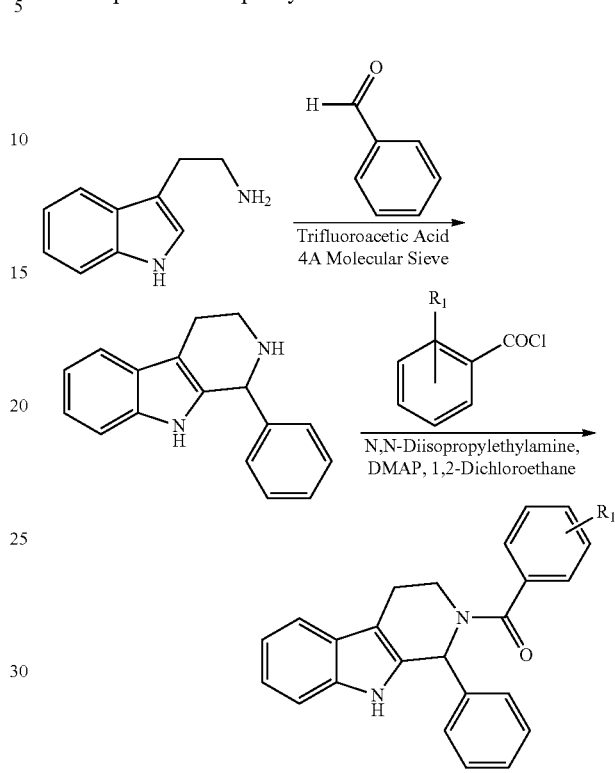

$R_1$ = H, p-CF$_3$, p-F, m-Me, p-CF$_3$, p-Me, pentyl-F, p-NO$_2$, p-NMe$_2$, p-CN, p,m-DiCl, p-OMe, p,o-DiCl, m,m-DiCl, o-Me, p-Cl, p-tBu Compounds with thiophene ring

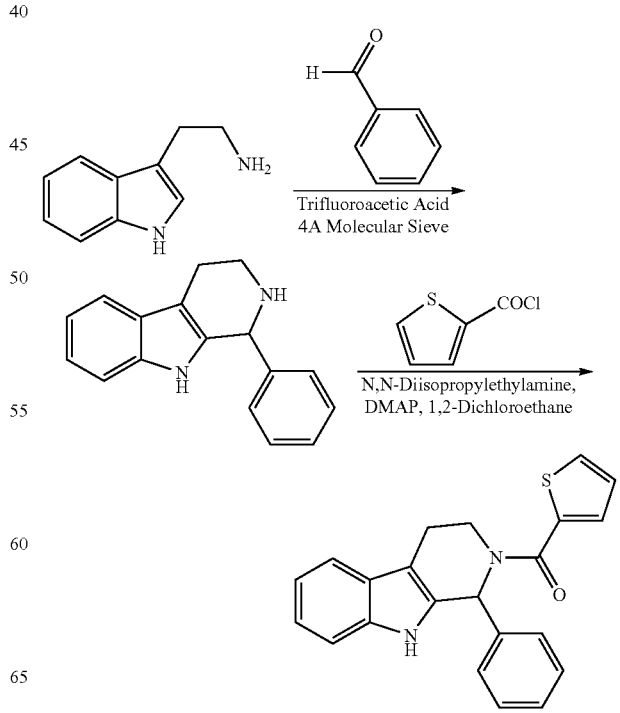

Example 2

Synthesis of Phenyl-(1-phenyl-1,3,4,9-tetrahydro-β-carbolin-2-yl)-methanone (compound MN341)

Example 2.1

1-Phenyl-2,3,4,9-tetrahydro-1H-β-carboline

A 500 ml round bottomed flask, equipped with a condenser and oil bath was charged with 10.0 g of tryptamine (1 eq.), 6.62 g (1 eq.) of benzaldehyde, 5 g of 4 Å molecular sieves (as a dehydrating agent) and 200 ml of 1,2-DCE. After dissolution, 2.85 g (0.4 eq.) of trifluoroacetic acid was added in one portion. The reaction mixture was brought to reflux. Completion of the reaction was monitored by TLC, after which the temperature was cooled to 30° C., followed by the removal of molecular sieves through a loose glass wool plug. The solution was quenched with 150 ml of saturated $NaHCO_3$ aqueous solution and diluted with 500 ml of ethyl acetate. The organic layer was separated, washed with brine and dried with $MgSO_4$. After the solvent was removed, flash chromatography (10% $CH_3OH/CH_2Cl_2$) allowed isolation of the title product (3.1 g, 20%) as a solid.

Example 2.2

Phenyl-(1-phenyl-1,3,4,9-tetrahydro-β-carbolin-2-yl)-methanone 0.2 g of 1-Phenyl-2,3,4,9-tetrahydro-1H-β-carboline (1 eq.) and 0.4 ml of N,N-diisopropylethylamine (2.8 eq.) were dissolved with 8 ml of 1,2-DCE in a scintillation vial. 0.281 g of Benzoyl chloride (2.5 eq.) and 6.7 mg of 4-dimethylaminopyridine (0.07 eq.) were dissolved with 1 ml of 1,2-DCE in another scintillation vial. These two solutions were mixed together, sealed and stirred overnight. Completion of the reaction was monitored by TLC, after which 2 ml of 10% citric acid aqueous solution was added to the reaction mixture. The solution was diluted with 50 ml of ethyl acetate. The organic layer was separated, washed twice with 10 ml of saturated $NaHCO_3$ aqueous solution, brine and dried with $MgSO_4$. After the solvent was removed, flash chromatography allowed isolation of the title product (0.24 g, 86%) as a solid.

C. Synthesis Schemes for Compounds MN359-MN378

Compound with phenyl substitution

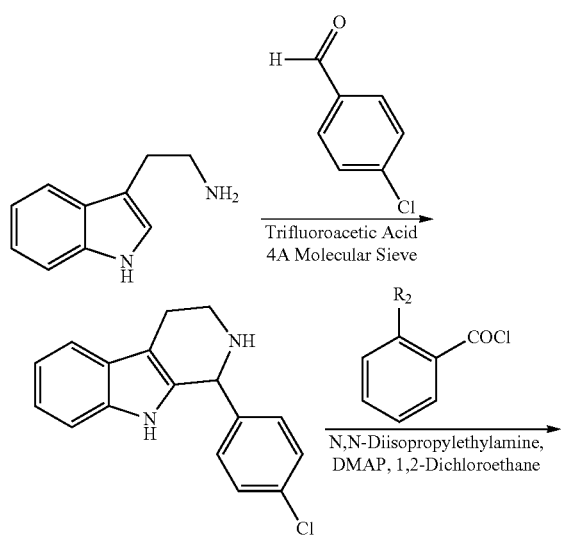

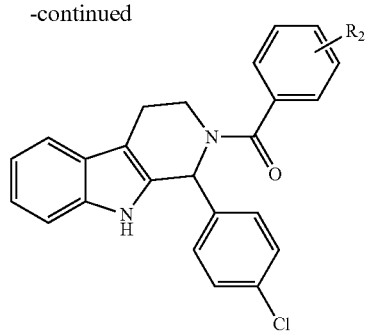

$R_2$ = H, p-$CF_3$, p-F, m-Me, m-$CF_3$, p-Me, pentyl-F, p-$NO_2$, p-$NMe_2$, p-CN, p,m-DiCl, p-OMe, p,o-DiCl, m,m-DiCl, o-Me, p-Cl, p-$^t$Bu, m-Cl, m,o-DiCl Compound with thiophene ring

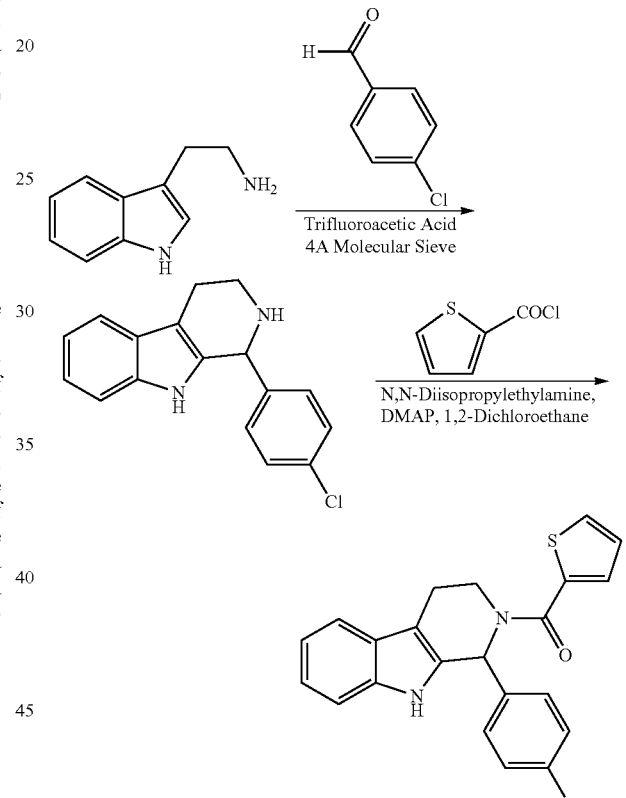

Example 3

[1-(4-Chloro-phenyl)-1,3,4,9-tetrahydro-β-carbolin-2-yl]-phenyl-methanone (compound MN359)

Example 3.1

1-(4-Chloro-phenyl)-2,3,4,9-tetrahydro-1H-β-carboline

A 500 ml round bottomed flask, equipped with a condenser and oil bath was charged with 10.0 g of tryptamine (1 eq.), 8.77 g (1 eq.) of 4-chlorobenzaldehyde, 5 g of 4 Å molecular sieves (as a dehydrating agent) and 200 ml of 1,2-DCE. After dissolution, 2.85 g (0.4 eq.) of trifluoroacetic acid was added in one portion. The reaction mixture was brought to reflux. Completion of the reaction was monitored by TLC, after which the temperature was cooled to 30° C., followed by the removal of molecular sieves through a loose glass wool plug. The solution was quenched with 150 ml of saturated NaHCO₃ aqueous solution and diluted with 500 ml of ethyl acetate. The organic layer was separated, washed with brine and dried with MgSO₄. After the solvent was removed, flash chromatography (10% CH₃OH/CH₂Cl₂) allowed isolation of the title product (7.8 g, 32%) as a solid.

Example 3.2

[1-(4-Chloro-phenyl)-1,3,4,9-tetrahydro-β-carbolin-2-yl]-phenyl-methanone 0.2 g of 1-(4-Chloro-phenyl)-2,3,4,9-tetrahydro-1H-β-carboline (1 eq.), 0.46 ml of N,N-diisopropylethylamine (3.7 eq.) and 23 mg of 4-dimethylaminopyridine (0.27 eq.) were dissolved with 8 ml of 1,2-DCE in a scintillation vial. 0.28 g of Benzoyl chloride (2.8 eq.) was dissolved with 1 ml of 1,2-DCE in another scintillation vial. These two solutions were mixed together, sealed and stirred overnight. Completion of the reaction was monitored by TLC, after which 2 ml of 10% citric acid aqueous solution was added to the reaction mixture. The solution was diluted with 50 ml of ethyl acetate. The organic layer was separated, washed twice with 10 ml of saturated NaHCO₃ aqueous solution, brine and dried with MgSO₄. After the solvent was removed, flash chromatography allowed isolation of the title product (0.24 g, 87%) as a solid.

D. Synthesis Schemes for MN379-MN398

Compound with phenyl substitution

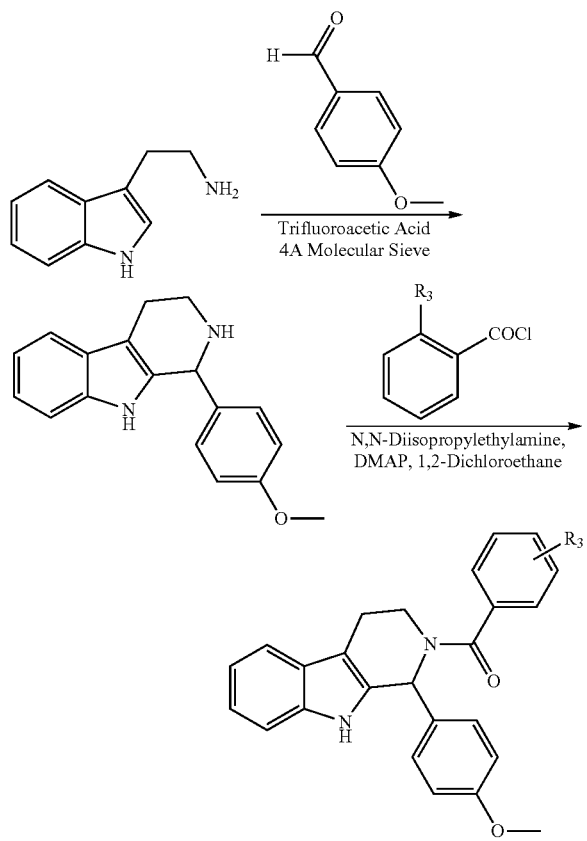

R₃ = H, p-CF₃, p-F, m-Me, m-CF₃, p-Me, pentyl-F, p-NO₂, p-NMe₂, p-CN, p,m-DiCl, p-OMe, p,o-DiCl, m,m-DiCl, o-Me, p-Cl, p-ᵗBu, m-Cl, m,o-DiCl Compound with thiophene ring

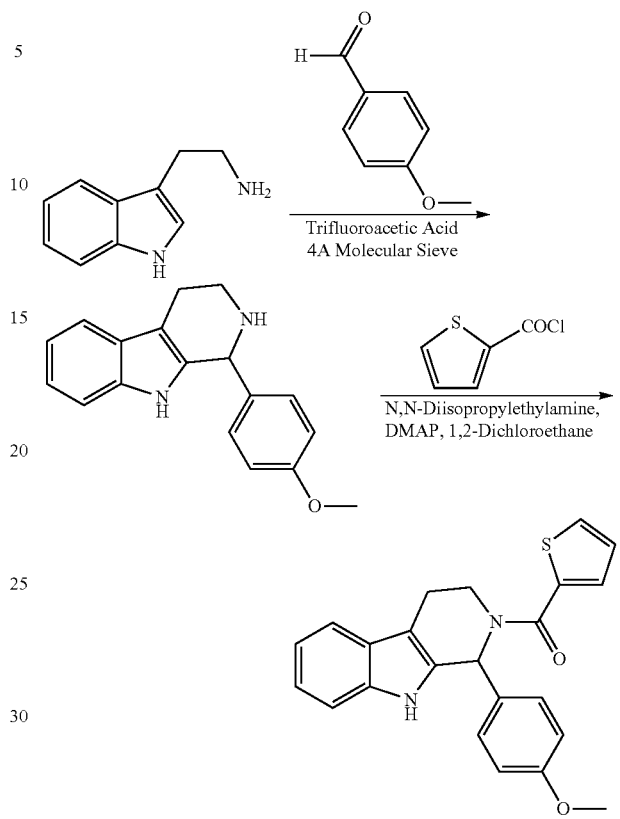

Example 4

[1-(4-Methoxy-phenyl)-1,3,4,9-tetrahydro-β-carbolin-2-yl]-phenyl-methanone (compound MN379)

Example 4.1 1-(4-Methoxy-phenyl)-2,3,4,9-tetrahydro-1H-β-carboline

A 500 ml round bottomed flask, equipped with a condenser and oil bath was charged with 10.0 g of tryptamine (1 eq.), 8.5 g (1 eq.) of 4-methoxybenzaldehyde, 5 g of 4 A molecular sieves (as a dehydrating agent) and 200 ml of 1,2-DCE. After dissolution, 2.85 g (0.4 eq.) of trifluoroacetic acid was added in one portion. The reaction mixture was brought to reflux. Completion of the reaction was monitored by TLC, after which the temperature was cooled to 30° C., followed by the removal of molecular sieves through a loose glass wool plug. The solution was quenched with 150 ml of saturated NaHCO₃ aqueous solution and diluted with 500 ml of ethyl acetate. The organic layer was separated, washed with brine and dried with MgSO₄. After the solvent was removed, flash chromatography (10% CH₃OH/CH₂Cl₂) allowed isolation of the title product (12.8 g, 54%) as a solid.

Example 4.2

[1-(4-Methoxy-phenyl)-1,3,4,9-tetrahydro-β-carbolin-2-yl]-phenyl-methanone 0.2 g of 1-(4-Methoxy-phenyl)-2,3,4,9-tetrahydro-1H-β-carboline (1 eq.), 0.46 ml of N,N-diisopropylethylamine (3.7 eq.) and 3.2 mg of 4-dimethylaminopyridine (0.2 eq.) were dissolved with 8 ml of 1,2-DCE in a scintillation vial. 0.113 g of Benzoyl chloride (1.12 eq.) was dissolved with 1 ml of 1,2-DCE in another scintillation vial. These two solutions were mixed together, sealed and stirred overnight. Completion of the reaction was monitored by TLC, after which 2 ml of 10% citric acid aqueous solution was added to the reaction mixture. The solution was diluted with 50 ml of ethyl acetate. The organic layer was separated, washed twice with 10 ml of saturated NaHCO₃ aqueous solution, brine and dried with MgSO₄. After the solvent was removed, flash chromatography allowed isolation of the title product (0.21 g, 76%) as a solid.

E. Synthesis Schemes for Other Chemotype 4 Compounds

Compound with phenyl substitution

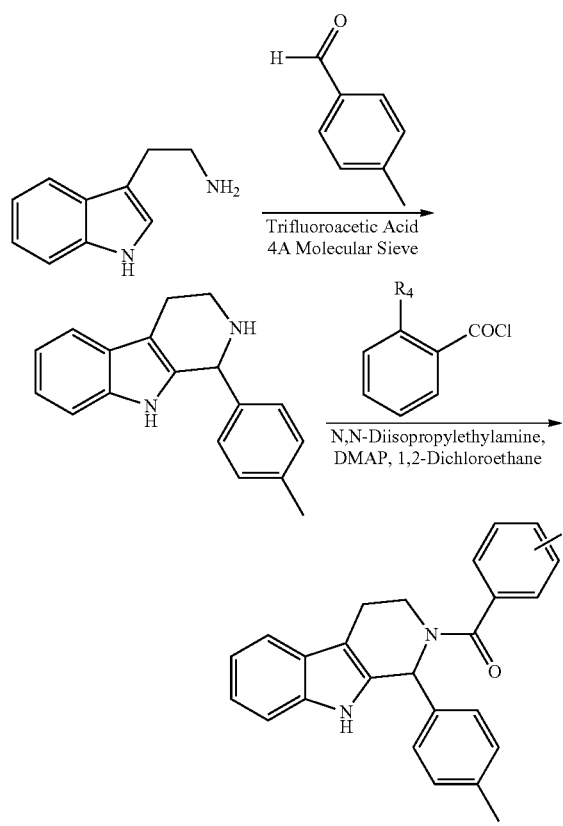

R₄ = p-Me, H, p-OMe, p-Cl, p-CF₃, p-F, m-Me, m-CF₃, p-Me, pentyl-F, p-NO₂, p-NMe₂, p-CN, p,m-DiCl, p,o-DiCl, m,m-DiCl, o-Me, p-Cl, p-ᵗBu Compound with thiophene ring

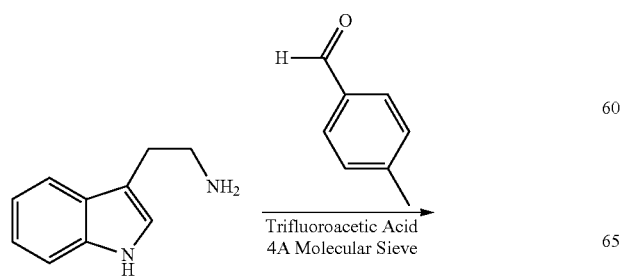

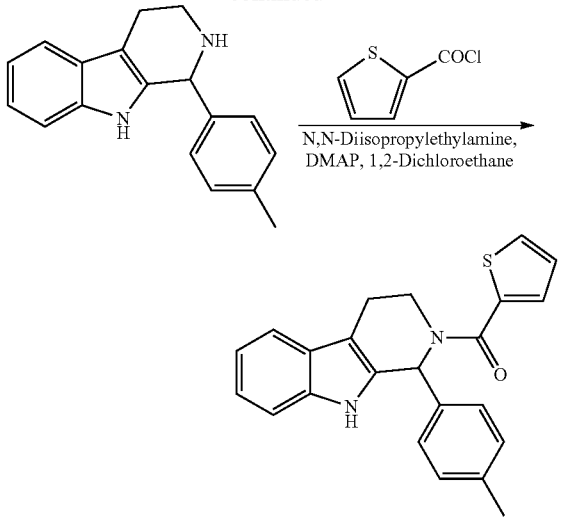

Compound with cyclopentyl ring

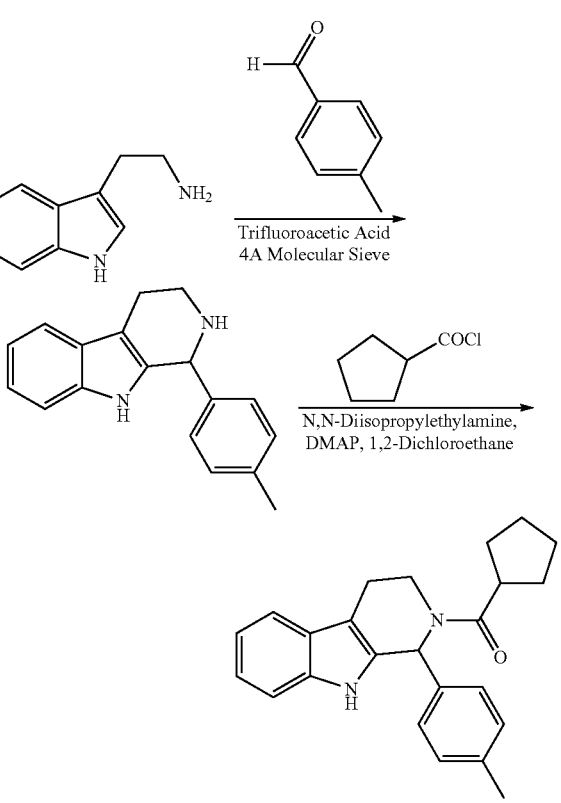

Example 5 p-Tolyl-(1-p-tolyl-1,3,4,9-tetrahydro-β-carbolin-2-yl)-methanone (compound 132C9)

Example 5.1

1-p-Tolyl-2,3,4,9-tetrahydro-1H-β-carboline

A dry 250 ml round bottomed flask, equipped with a condenser and oil bath was charged with 5.0 g of tryptamine (1 eq.), 3.7 g (1 eq.) of p-tolualdehyde, 2.5 g of 4 A molecular sieves (as a dehydrating agent) and 100 ml of 1,2-DCE. After dissolution, 1 ml (0.4 eq.) of trifluoroacetic acid was added in one portion. The reaction mixture was brought to reflux. Completion of the reaction was monitored by TLC, after which the temperature was cooled to 30° C., followed by the removal of molecular sieves through a loose glass wool plug. The solution was quenched with 50 ml of saturated $NaHCO_3$ aqueous solution and diluted with 200 ml of ethyl acetate. The organic layer was separated, washed with brine and dried with $MgSO_4$. After the solvent was removed, flash chromatography (10% $CH_3OH/CH_2Cl_2$) allowed isolation of the title product (7.6 g, 93%) as a solid.

Example 5.2 p-Tolyl-(1-p-tolyl-1,3,4,9-tetrahydro-β-carbolin-2-yl)-methanone

An oven-dried 250 ml round bottom flask, equipped with a stir bar was charged 1 g of 1-p-Tolyl-2,3,4,9-tetrahydro-1H-β-carboline (1 eq.), 10 mg of 4-dimethylaminopyridine (catalyze amount) and 40 ml of 1,2-DCE. The flask was sealed under Argon. Then 1.3 ml of N,N-diisopropylethyl-amine (2 eq.) and 0.62 g of p-toluoyl chloride (1.05 eq.) were sequentially added into reaction mixture. Completion of the reaction was monitored by TLC, after which 2 ml of THF and 10 ml of saturated $NaHCO_3$ aqueous solution were added. The stirring was continued for one more hour. The solution was diluted with 200 ml of ethyl acetate. The organic layer was separated, washed twice with 30 ml of saturated $NaHCO_3$ aqueous solution, brine and dried with $NaSO_4$. After the solvent was removed, flash chromatography allowed isolation of the title product (0.7 g, 49%) as a white solid.

Example 6

Effect of Compounds on Tumor Cells

The following experimental procedure was used to obtain the results pictured in FIG. 1A-D. HEK293 cells (MUC1-negative-ATCC HTB-133) or T47D cells (MUC1 and MUC1*-positive-ATCC CRL-1573) were plated at 20,000 cells/well in 96 well plates, at a final volume of 100 microliters. HEK293 cells were maintained and plated in DMEM medium with 10% serum, and T47D cells were maintained and plated in complete RPMI medium with 10% serum. Cells were plated in triplicate for each experimental condition. The day after plating, compounds were added at final concentrations of 0, 2.5 μM, 5 μM, and 10M. This was done by adding 1 microliter of 250 μM, 500 μM, or 1 mM stock concentrations of compounds. The zero compound control was the addition of 1 microliter of DMSO alone. These were prepared from 10 mM stocks of compounds which were dissolved from their solid form in DMSO at room temperature. Solutions of compounds (250 μM, 500 μM, 1 mM, or 10 mM stocks) or DMSO for zero compound controls were stored at −20 C. 48 hours after the addition of compounds to cells, cells were resuspended in 50 microliters of Trypsin-EDTA, and counted using a hemocytometer. To determine the effect of the test compound on the growth of MUC 1-positive cells verses MUC1-negative cells, cell counts for each cell line were plotted, as was the difference, or "delta" between them (Delta=HEK293 cell counts minus T47D cell counts). Graphs were plotted using Microsoft Excel. FIGS. 1A-D shows the effect of each compound at a final concentration of 5 uM.

Example 7

Figure 2:
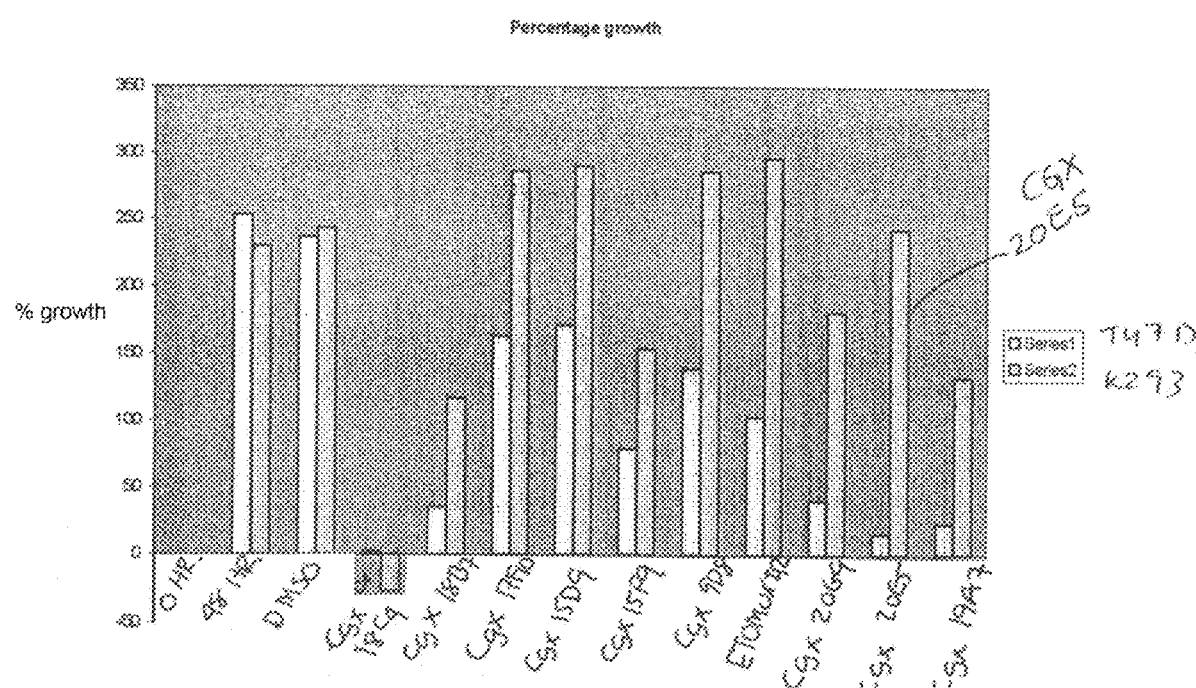
FIG. 2 is a bar graph showing the effects of various compounds on the growth of either MUC1/MUC1* positive cancer cells (T47D) or on MUC1-negative control cells (HEK293 also called K293). The amount of cell growth has been normalized wherein the amount that each cell type grew when DMSO alone is added, is defined as 100%.

The Effect of Various Compounds on the Growth of MUC1-Positive Cancer Cells and MUC 1-Negative Cells The bar graph shown in FIG. 2 was drawn from results obtained using the following experimental procedure. This procedure is also the one that was used to obtain the percent growth numbers for compounds MN400-MN410, the chemical structures of which are shown in the application. HEK293 cells (also called K293, ATCC HTB-133) were plated at 5,000 cells/well, and T47D cells (ATCC CRL-1573) were plated at 10,000 cells/well in 96 well plates, at a final volume of 100 microliters. HEK293 cells were maintained and plated in DMEM medium with 10% serum, and T47D were maintained and plated in complete RPMI medium with 10% serum. Cells were plated in triplicate for each experimental condition. The day after plating, zero day counts were taken by resuspending cells in 50 microliters of Trypsin-EDTA and a hemocytometer. Then, compounds were added at a final concentration of 30 μM. This was done by adding 1 microliter of 3 mM stock concentration of compounds. Zero compound controls was the addition of 1 microliter of DMSO alone. Solutions of compounds or DMSO for zero compound controls were stored at −20 C. 48 hours after the addition of compounds to cells, cells were resuspended in 50 microliters of Trypsin-EDTA, and counted using a hemocytometer. Percent Normalized Growth was then calculated: Percent Normalized Growth= [(48 Hour cell counts with Compound Added)−(Zero-day cell counts)]/[(48 Hour Cell counts with DMSO added)−(Zero-day cell counts)]×100%. Results were then plotted using Microsoft Excel.

Example 8

Figure 3:
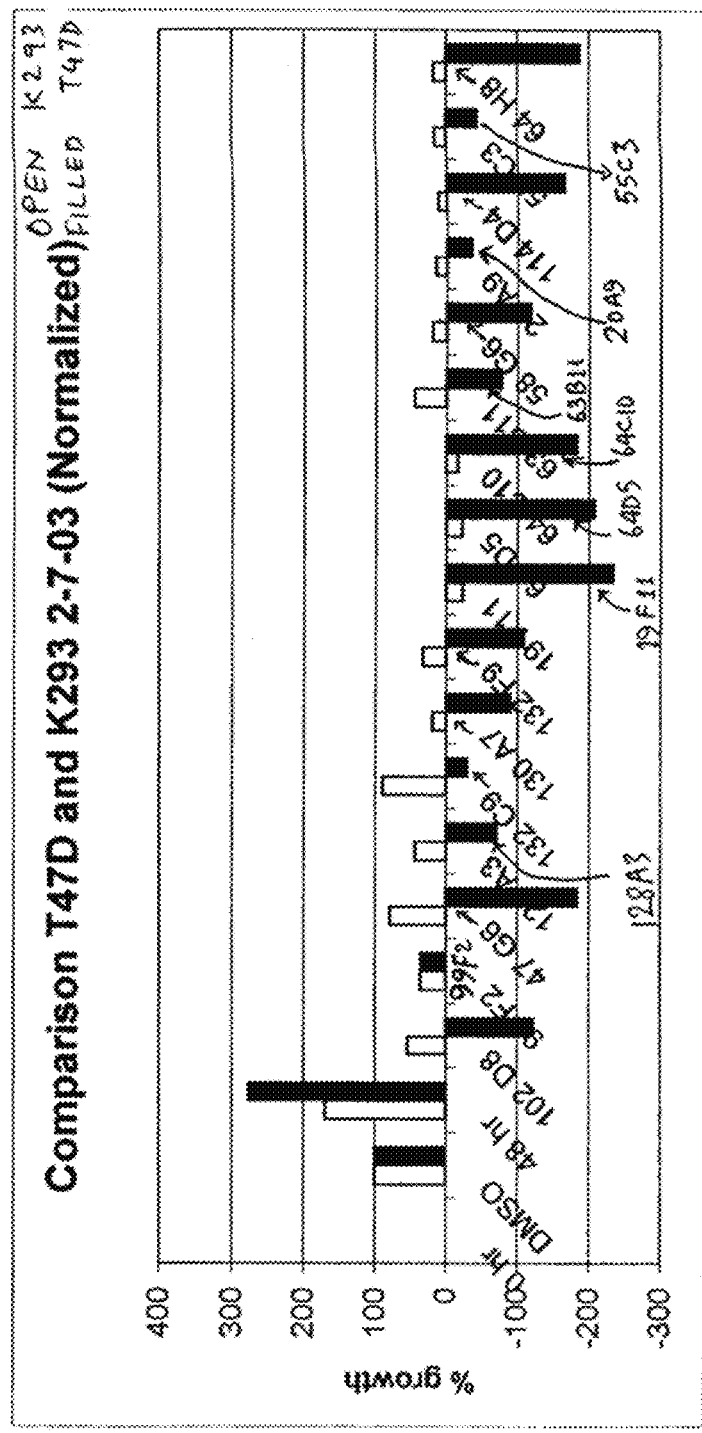
FIG. 3 is a bar graph showing the effects of various compounds on the growth of either MUC1/MUC1* positive cancer cells (T47D) or on MUC1-negative control cells (HEK293 also called K293). The percent cell growth is plotted.

The Effect of MUC1*-Targeting Compounds on the Growth of MUC1-Positive Verses MUC1-Negative Cells The bar graph shown in FIG. 3 were the results of compound screening obtained using the following experimental procedure. HEK293 cells (also called K293, ATCC HTB -133) or T47D cells (ATCC CRL-1573) were plated at 3,000 cells/well in 96 well plates, at a final volume of 100 microliters. HEK293 cells were maintained and plated in DMEM medium with 10% serum, and T47D cells were maintained and plated in complete RPMI medium with 10% serum. Cells were plated in triplicate for each experimental condition. The day after plating, zero day counts were taken by resuspending cells in 50 microliters of Trypsin-EDTA and a hemocytometer. Then, compounds were added at a final concentration of 30 μM. This was done by adding 1 microliter of 3 mM stock concentration of compounds. Zero compound controls refer to the addition of either 1 microliter of DMSO alone, or no addition at all. Solutions of compounds or DMSO for zero compound controls were stored at −20 C. 48 hours after the addition of compounds to cells, cells were resuspended in 50 microliters of Trypsin-EDTA, and counted using a hemocytometer. Percent Growth was then calculated: Percent Growth=(48 Hour cell counts with Compound Added)/(48 Hour Cell counts with DMSO alone added)×100%. Results were then plotted using Microsoft Excel.

All of the references cited herein are incorporated by reference in their entirety.

Those skilled in the art will recognize, or be able to ascertain using no more than routine experimentation, many equivalents to the specific embodiments of the invention specifically described herein. Such equivalents are intended to be encompassed in the scope of the claims.

TABLE 1

Peptide sequences (listed from N-terminus to C-terminus):

Full-length MUC1 Receptor (Mucin 1 precursor, Genbank Accession number: P15941)
(SEQ ID NO: 1)
MTPGTQSPFF LLLLLTVLTV VTGSGHASST PGGEKETSAT
QRSSVPSSTE KNAVSMTSSV LSSHSPGSGS STTQGQDVTL
APATEPASGS AATWGQDVTS VPVTRPALGS TTPPAHDVTS
APDNKPAPGS TAPPAHGVTS APDTRPAPGS TAPPAHGVTS
APDTRPAPGS TAPPAHGVTS APDTRPAPGS TAPPAHGVTS
APDTRPAPGS TAPPAHGVTS APDTRPAPGS TAPPAHGVTS
APDTRPAPGS TAPPAHGVTS APDTRPAPGS TAPPAHGVTS
APDTRPAPGS TAPPAHGVTS APDTRPAPGS TAPPAHGVTS
APDTRPAPGS TAPPAHGVTS APDTRPAPGS TAPPAHGVTS
APDTRPAPGS TAPPAHGVTS APDTRPAPGS TAPPAHGVTS
APDTRPAPGS TAPPAHGVTS APDTRPAPGS TAPPAHGVTS
APDTRPAPGS TAPPAHGVTS APDTRPAPGS TAPPAHGVTS
APDTRPAPGS TAPPAHGVTS APDTRPAPGS TAPPAHGVTS
APDTRPAPGS TAPPAHGVTS APDTRPAPGS TAPPAHGVTS
APDTRPAPGS TAPPAHGVTS APDTRPAPGS TAPPAHGVTS
APDTRPAPGS TAPPAHGVTS APDTRPAPGS TAPPAHGVTS
APDTRPAPGS TAPPAHGVTS APDTRPAPGS TAPPAHGVTS
APDTRPAPGS TAPPAHGVTS APDTRPAPGS TAPPAHGVTS
APDTRPAPGS TAPPAHGVTS APDTRPAPGS TAPPAHGVTS
APDTRPAPGS TAPPAHGVTS APDTRPAPGS TAPPAHGVTS
APDTRPAPGS TAPPAHGVTS APDNRPALGS TAPPVHNVTS
ASGSASGSAS TLVHNGTSAR ATTTPASKST PFSIPSHHSD
TPTTLASHST KTDASSTHHS SVPPLTSSNH STSPQLSTGV
SFFFLSFHIS NLQFNSSLED PSTDYYQELQ RDISEMFLQI
YKQGGFLGLS NIKFRPGSVV VQLTLAFREG TINVHDVETQ
FNQYKTEAAS RYNLTISDVS VSDVPFPFSA QSGAGVPGWG
IALLVLVCVL VALAIVYLIA LAVCQCRRKN YGQLDIFPAR
DTYHPMSEYP TYHTHGRYVP PSSTDRSPYE KVSAGNGGSS
LSYTNPAVAA ASANL N-terminal MUC-1 signaling sequence for directing MUC1 receptor and truncated isoforms to cell membrane surface. Up to 3 amino acid residues may be absent at C-terminal end as indicated by variants in SEQ ID NOS: 2, 3 and 4.
(SEQ ID NO: 2)
MTPGTQSPFFLLLLLTVLT.
(SEQ ID NO: 3)
MTPGTQSPFFLLLLLTVLT VVTA
(SEQ ID NO: 4)
MTPGTQSPFFLLLLLTVLT VVTG A truncated MUC1 receptor isoform having nat-PSMGFR at its N-terminus and including the transmembrane and cytoplasmic sequences of a full-ength MUC1 receptor ("nat-PSMGFRTC isoform"-An example of "PSMGFRTC"-shown excluding optional N-terminus signal sequence, which may be cleaved after translation and prior to expression of the receptor on the cell surface):
(SEQ ID NO: 5)
G TINVHDVETQ FNQYKTEAAS RYNLTISDVS VSDVPFPFSA
QSGAGVPGWG IALLVLVCVL VALAIVYLIA LAVCQCRRKN
YGQLDIFPAR DTYHPMSEYP TYHTHGRYVP PSSTDRSPYE
KVSAGNGGSS LSYTNPAVAA ASANL TABLE 1-continued Peptide sequences (listed from N-terminus to C-terminus):

A truncated MUC1 receptor isoform having nat-PSMGFR and PSIBR at its N-terminus and including the transmembrane and cytoplasmic sequences of a full-length MUC1 receptor ("CM isoform"-shown excluding optional N-terminus signal sequence, which may be cleaved after translation and prior to expression of the receptor on the cell surface):
(SEQ ID NO: 6)
GFLGLS NIKFRPGSVV VQLTLAFREG TINVHDVETQ FNQYKTEAAS
RYNLTISDVS VSDVPFPFSA QSGAGVPGWG IALLVLVCVL
VALAIVYLIA LAVCQCRRKN YGQLDIFPAR DTYHPMSEYP
TYHTHGRYVP PSSTDRSPYE KVSAGNGGSS LSYTNPAVAA ASANL A truncated MUC1 receptor isoform having nat-SMGFR + PSIBR + Unique Region at its N-terminus and including the transmembrane and cytoplasmic sequences of a full-length MUC1 receptor ("UR isoform"-shown excluding optional N-terminus signal sequences):
(SEQ ID NO: 7)
ATTTPASKST PFSIPSHHSD TPTTLASHST KTDASSTHHS
TVPPLTSSNH STSPQLSTGV SFFFLSFHIS NLQFNSSLED
PSTDYYQELQ RDISEMFLQI YKQGGFLGLS NIKFRPGSVV
VQLTLAFREG TINVHDVETQ FNQYKTEAAS RYNLTISDVS
VSDVPFPFSA QSGAGVPGWG IALLVLVCVL VALAIVYLIA
LAVCQCRRKN YGQLDIFPAR DTYHPMSEYP TYHTHGRYVP
PSSTDRSPYE KVSAGNGGSS LSYTNPAVAA ASANL A truncated MUC1 receptor isoform including the transmembrane and cytoplasmic sequences of a full-length MUC1 receptor ("Y isoform"-shown excluding optional N-terminus signal sequence, which may be cleaved after translation and prior to expression of the receptor on the cell surface):
(SEQ ID NO: 8)
GSGHASSTPG GEKETSATQR SSVPSSTEKN AFNSSLEDPS
TDYYQELQRD ISEMFLQIYK QGGFLGLSNI KFRPGSVVVQ
LTLAFREGTI NVHDMETQFN QYKTEAASRY NLTISDVSVS
DVPFPFSAQS GAGVPGWGIA LLVLVCVLVA LAIVYLIALA
VCQCRRKNYG QLDIFPARDT YHPMSEYPTY HTHGRYVPPS
STDRSPYEKV SAGNGGSSLS YTNPAVAATS ANL A truncated MUC1 receptor isoform having nat-PSMGFR + PSIBR + Unique Region + Repeats at its N-terminus and including the transmembrane and cytoplasmic sequences of a full-length MUC1 receptor ("Rep isoform"-shown excluding optional N-terminus signal sequence, which may be cleaved after translation and prior to expression of the receptor on the cell surface):
(SEQ ID NO: 9)
LDPRVRTSAP DTRPAPGSTA PQAHGVTSAP DTRPAPGSTA
PPAHGVTSAP DTRPAPGSTA PPAHGVTSAP DTRPAPGSTA
PPAHGVTSAP DTRPAPGSTA PPAHGVTSAP DTRPAPGSTA
PPAHGVTSAP DTRPAPGSTA PPAHGVTSAP DTRPAPGSTA
PPAHGVTSAP DTRPAPGSTA PPAHGVTSAP DTRPAPGSTA
PPAHGVTSAP DTRPAPGSTA PPAHGVTSAP DTRPAPGSTA
PPAHGVTSAP DTRPAPGSTA PPAHGVTSAP DTRPAPGSTA
PPAHGVTSAP DTRPAPGSTA PPAHGVTSAP DTRPAPGSTA
PPAHGVTSAP DTRPAPGSTA PPAHGVTSAP DTRPAPGSTA
PPAHGVTSAP DTRPAPGSTA PPAHGVTSAP DTRPAPGSTA
PPAHGVTSAP DTRPAPGSTA PPAHGVTSAP DTRPAPGSTA
PPAHGVTSAP DTRPAPGSTA PPAHGVTSAP DTRPAPGSTA
PPAHGVTSAP DTRPAPGSTA PPAHGVTSAP DTRPAPGSTA
PPAHGVTSAP DTRPAPGSTA PPAHGVTSAP DNRPALGSTA
PPVHNVTSAS GSASGSASTL VHNGTSARAT TTPASKSTPF
SIPSHHSDTP TTLASHSTKT DASSTHHSSV PPLTSSNHST
SPQLSTGVSF FFLSFHISNL QFNSSLEDPS TDYYQELQRD
ISEMFLQIYK QGGFLGLSNI KFRPGSVVVQ LTLAFREGTI
NVHDVETQFN QYKTEAASRY NLTISDVSVS DVPFPFSAQS
GAGVPGWGIA LLVLVCVLVA LAIVYLIALA VCQCRRKNYG
QLDIFPARDT YHPMSEYPTY HTHGRYVPPS STDRSPYEKV
SAGNGGSSLS YTNPAVAAAS ANL

TABLE 1-continued

Peptide sequences (listed from N-terminus to C-terminus):

Native Primary Sequence of the MUC1 Growth Factor Receptor (nat-PSMGFR-an example of "PSMGFR"):
(SEQ ID NO: 10)
GTINVHDVETQFNQYKTEAASRYNLTISDVSVSDVPFPFSAQSGA Native Primary Sequence of the MUC1 Growth Factor Receptor (nat-PSMGFR-An example of "PSMGFR"), having a single amino acid deletion at the N-terminus of SEQ ID NO: 10):
(SEQ ID NO: 11)
TINVHDVETQFNQYKTEAASRYNLTISDVSVSDVPFPFSAQSGA "SPY" functional variant of the native Primary Sequence of the MUC1 Growth Factor Receptor having enhanced stability (var-PSMGFR-An example of "PSMGFR"):
(SEQ ID NO: 12)
GTINVHDVETQFNQYKTEAASPYNLTISDVSVSDVPFPFSAQSGA "SPY" functional variant of the native Primary Sequence of the MUC1 Growth Factor Receptor having enhanced stability (var-PSMGFR-An example of "PSMGFR"), having a single amino acid deletion at the C-terminus of SEQ ID NO: 12):
(SEQ ID NO: 13)
TINVHDVETQFNQYKTEAASPYNLTISDVSVSDVPFPFSAQSGA Truncated PSMGFR receptor (TR) (having "SPY" sequence of var-PSMGFR):
(SEQ ID NO: 14)
GTINVHDVETQFNQYKTEAASPYNLTISDVSVS Extended Sequence of MUC1 Growth Factor Receptor (ESMGFR) (having "SPY" sequence of var-PSMGFR):
(SEQ ID NO: 15)
VQLTLAFREGTINVHDVETQFNQYKTEAASPYNLTISDVSVSDVPFPF Tumor-Specific Extended Sequence of MUC1 Growth Factor Receptor (TSESMGFR) (having "SPY" sequence of var-PSMGFR):
(SEQ ID NO: 16)
SVVVQLTLAFREGTINVHDVETQFNQYKTEAASPYNLTISDVSVSDVPFPFSAQSGA Primary Sequence of the Interchain Binding Region) (PSIBR):
(SEQ ID NO: 17)
GFLGLSNIKFRPGSVVVQLTLAFRE Truncated Interchain Binding Region) (TPSIBR):
(SEQ ID NO: 18)
SVVVQLTLAFREG Repeat Motif 2 (RM2):
(SEQ ID NO: 19)
PDTRPAPGSTAPPAHGVTSAPDTRPAPGSTAPPAHGVTSA

---

What is claimed is:

1. A method for treating cancer in which cancerous cells express MUC1* in a subject comprising assaying for presence of MUC1* in the cancer cells, and administering a treatment effective amount of a compound comprised of the formula below to the subject in which cancer cells express MUC1*:

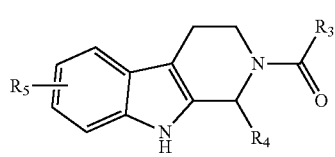

(III)

or a steroisomer, tautomer, pharmaceutically acceptable salt, or ester thereof, wherein,
- R3 is carbocycloalkyl;
- R4 is selected from alkyl, branched alkyl, cycloalkyl, and H; and
- R5 is halogen, lower alkyl, haloalkyl, alkylether, —NH$_2$, mono-substituted amine, di-substituted amine, cyclic amine, or H.

2. The method according to claim 1, wherein R5 is selected from halogen, lower alkyl, haloalkyl, alkylether, and H.

3. The method according to claim 1, wherein R5 is H, F, Cl, OCH$_3$, CH$_3$, CN, NO$_2$, or NH$_2$.

4. The method according to claim 1, wherein R5 is selected from H, F, and Cl.

5. The method according to claim 1, wherein R5 is H.

6. A method for treating cancer in which cancerous cells express MUC1* in a subject comprising assaying for presence of MUC1* in the cancer cells, and administering a treatment effective amount of a compound comprised of the formula below to the subject in which cancer cells express MUC1*:

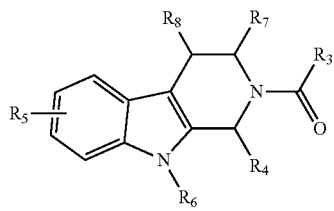

(IV)

or a steroisomer, tautomer, pharmaceutically acceptable salt, or ester thereof, wherein,
- R3 is carbocycloalkyl;
- R4 is selected from alkyl, branched alkyl, cycloalkyl, and H;
- R5 is halogen, lower alkyl, haloalkyl, alkylether, —NH$_2$, mono-substituted amine, di-substituted amine, cyclic amine, or H;
- R6 is H or alkyl;
- R7 is H or alkyl; and
- R8 is H or alkyl.

7. The method according to claim 6, wherein R5 is selected from halogen, lower alkyl, haloalkyl, alkylether, and H.

8. The method according to claim 6, wherein R5 is H, F, Cl, OCH$_3$, CH$_3$, CN, NO$_2$, or NH$_2$.

9. The method according to claim 6, wherein
R5 is H, F, or Cl;
R6 is H or CH$_3$;
R7 is H or CH$_3$; and
R8 is H or CH$_3$.

10. The method according to claim 6, wherein
R5 is H;
R6 is H;
R7 is H; and
R8 is H.

11. The method according to claim 1, wherein R5 is is morpholine, pyrrolidine, piperazine or piperidine.

12. The method according to claim 1, wherein R5 is —OCH$_3$.

13. The method according to claim 2, wherein R5 is F, Cl, Br or I.

14. The method according to claim 2, wherein R5 is CF3.

15. The method according to claim 2, wherein R5 is methyl, ethyl or propyl.

16. The method according to claim 6, wherein R5 is morpholine, pyrrolidine, piperazine or piperidine.

17. The method according to claim 6, wherein R5 is —OCH$_3$.

18. The method according to claim 7, wherein R5 is CF3.

19. The method according to claim 7, wherein R5 is methyl, ethyl or propyl.

20. The method according to claim 7, wherein R5 is —OCH$_3$.

* * * * *

SEQUENCE LISTING

```
<160> NUMBER OF SEQ ID NOS: 19

<210> SEQ ID NO 1
<211> LENGTH: 1255
<212> TYPE: PRT
<213> ORGANISM: Artificial Sequence
<220> FEATURE:
<223> OTHER INFORMATION: Full-length MUC1 Receptor

<400> SEQUENCE: 1
```

Met Thr Pro Gly Thr Gln Ser Pro Phe Phe Leu Leu Leu Leu Thr
1               5                   10                  15

Val Leu Thr Val Val Thr Gly Ser Gly His Ala Ser Ser Thr Pro Gly
            20                  25                  30

Gly Glu Lys Glu Thr Ser Ala Thr Gln Arg Ser Ser Val Pro Ser Ser
        35                  40                  45

Thr Glu Lys Asn Ala Val Ser Met Thr Ser Ser Val Leu Ser Ser His
    50                  55                  60

Ser Pro Gly Ser Gly Ser Ser Thr Thr Gln Gly Gln Asp Val Thr Leu
65                  70                  75                  80

Ala Pro Ala Thr Glu Pro Ala Ser Gly Ser Ala Ala Thr Trp Gly Gln
                85                  90                  95

Asp Val Thr Ser Val Pro Val Thr Arg Pro Ala Leu Gly Ser Thr Thr
            100                 105                 110

Pro Pro Ala His Asp Val Thr Ser Ala Pro Asp Asn Lys Pro Ala Pro
        115                 120                 125

Gly Ser Thr Ala Pro Pro Ala His Gly Val Thr Ser Ala Pro Asp Thr
    130                 135                 140

Arg Pro Ala Pro Gly Ser Thr Ala Pro Pro Ala His Gly Val Thr Ser
145                 150                 155                 160

-continued

```
Ala Pro Asp Thr Arg Pro Ala Pro Gly Ser Thr Ala Pro Pro Ala His
                165                 170                 175
Gly Val Thr Ser Ala Pro Asp Thr Arg Pro Ala Pro Gly Ser Thr Ala
            180                 185                 190
Pro Pro Ala His Gly Val Thr Ser Ala Pro Asp Thr Arg Pro Ala Pro
        195                 200                 205
Gly Ser Thr Ala Pro Pro Ala His Gly Val Thr Ser Ala Pro Asp Thr
    210                 215                 220
Arg Pro Ala Pro Gly Ser Thr Ala Pro Pro Ala His Gly Val Thr Ser
225                 230                 235                 240
Ala Pro Asp Thr Arg Pro Ala Pro Gly Ser Thr Ala Pro Pro Ala His
                245                 250                 255
Gly Val Thr Ser Ala Pro Asp Thr Arg Pro Ala Pro Gly Ser Thr Ala
            260                 265                 270
Pro Pro Ala His Gly Val Thr Ser Ala Pro Asp Thr Arg Pro Ala Pro
        275                 280                 285
Gly Ser Thr Ala Pro Pro Ala His Gly Val Thr Ser Ala Pro Asp Thr
    290                 295                 300
Arg Pro Ala Pro Gly Ser Thr Ala Pro Pro Ala His Gly Val Thr Ser
305                 310                 315                 320
Ala Pro Asp Thr Arg Pro Ala Pro Gly Ser Thr Ala Pro Pro Ala His
                325                 330                 335
Gly Val Thr Ser Ala Pro Asp Thr Arg Pro Ala Pro Gly Ser Thr Ala
            340                 345                 350
Pro Pro Ala His Gly Val Thr Ser Ala Pro Asp Thr Arg Pro Ala Pro
        355                 360                 365
Gly Ser Thr Ala Pro Pro Ala His Gly Val Thr Ser Ala Pro Asp Thr
    370                 375                 380
Arg Pro Ala Pro Gly Ser Thr Ala Pro Pro Ala His Gly Val Thr Ser
385                 390                 395                 400
Ala Pro Asp Thr Arg Pro Ala Pro Gly Ser Thr Ala Pro Pro Ala His
                405                 410                 415
Gly Val Thr Ser Ala Pro Asp Thr Arg Pro Ala Pro Gly Ser Thr Ala
            420                 425                 430
Pro Pro Ala His Gly Val Thr Ser Ala Pro Asp Thr Arg Pro Ala Pro
        435                 440                 445
Gly Ser Thr Ala Pro Pro Ala His Gly Val Thr Ser Ala Pro Asp Thr
    450                 455                 460
Arg Pro Ala Pro Gly Ser Thr Ala Pro Pro Ala His Gly Val Thr Ser
465                 470                 475                 480
Ala Pro Asp Thr Arg Pro Ala Pro Gly Ser Thr Ala Pro Pro Ala His
                485                 490                 495
Gly Val Thr Ser Ala Pro Asp Thr Arg Pro Ala Pro Gly Ser Thr Ala
            500                 505                 510
Pro Pro Ala His Gly Val Thr Ser Ala Pro Asp Thr Arg Pro Ala Pro
        515                 520                 525
Gly Ser Thr Ala Pro Pro Ala His Gly Val Thr Ser Ala Pro Asp Thr
    530                 535                 540
Arg Pro Ala Pro Gly Ser Thr Ala Pro Pro Ala His Gly Val Thr Ser
545                 550                 555                 560
Ala Pro Asp Thr Arg Pro Ala Pro Gly Ser Thr Ala Pro Pro Ala His
                565                 570                 575
```

```
Gly Val Thr Ser Ala Pro Asp Thr Arg Pro Ala Pro Gly Ser Thr Ala
            580                 585                 590

Pro Pro Ala His Gly Val Thr Ser Ala Pro Asp Thr Arg Pro Ala Pro
        595                 600                 605

Gly Ser Thr Ala Pro Pro Ala His Gly Val Thr Ser Ala Pro Asp Thr
    610                 615                 620

Arg Pro Ala Pro Gly Ser Thr Ala Pro Pro Ala His Gly Val Thr Ser
625                 630                 635                 640

Ala Pro Asp Thr Arg Pro Ala Pro Gly Ser Thr Ala Pro Pro Ala His
                645                 650                 655

Gly Val Thr Ser Ala Pro Asp Thr Arg Pro Ala Pro Gly Ser Thr Ala
            660                 665                 670

Pro Pro Ala His Gly Val Thr Ser Ala Pro Asp Thr Arg Pro Ala Pro
        675                 680                 685

Gly Ser Thr Ala Pro Pro Ala His Gly Val Thr Ser Ala Pro Asp Thr
    690                 695                 700

Arg Pro Ala Pro Gly Ser Thr Ala Pro Pro Ala His Gly Val Thr Ser
705                 710                 715                 720

Ala Pro Asp Thr Arg Pro Ala Pro Gly Ser Thr Ala Pro Pro Ala His
                725                 730                 735

Gly Val Thr Ser Ala Pro Asp Thr Arg Pro Ala Pro Gly Ser Thr Ala
            740                 745                 750

Pro Pro Ala His Gly Val Thr Ser Ala Pro Asp Thr Arg Pro Ala Pro
        755                 760                 765

Gly Ser Thr Ala Pro Pro Ala His Gly Val Thr Ser Ala Pro Asp Thr
    770                 775                 780

Arg Pro Ala Pro Gly Ser Thr Ala Pro Pro Ala His Gly Val Thr Ser
785                 790                 795                 800

Ala Pro Asp Thr Arg Pro Ala Pro Gly Ser Thr Ala Pro Pro Ala His
                805                 810                 815

Gly Val Thr Ser Ala Pro Asp Thr Arg Pro Ala Pro Gly Ser Thr Ala
            820                 825                 830

Pro Pro Ala His Gly Val Thr Ser Ala Pro Asp Thr Arg Pro Ala Pro
        835                 840                 845

Gly Ser Thr Ala Pro Pro Ala His Gly Val Thr Ser Ala Pro Asp Thr
    850                 855                 860

Arg Pro Ala Pro Gly Ser Thr Ala Pro Pro Ala His Gly Val Thr Ser
865                 870                 875                 880

Ala Pro Asp Thr Arg Pro Ala Pro Gly Ser Thr Ala Pro Pro Ala His
                885                 890                 895

Gly Val Thr Ser Ala Pro Asp Thr Arg Pro Ala Pro Gly Ser Thr Ala
            900                 905                 910

Pro Pro Ala His Gly Val Thr Ser Ala Pro Asp Thr Arg Pro Ala Pro
        915                 920                 925

Gly Ser Thr Ala Pro Pro Ala His Gly Val Thr Ser Ala Pro Asp Asn
    930                 935                 940

Arg Pro Ala Leu Gly Ser Thr Ala Pro Val His Asn Val Thr Ser
945                 950                 955                 960

Ala Ser Gly Ser Ala Ser Gly Ser Ala Ser Thr Leu Val His Asn Gly
                965                 970                 975

Thr Ser Ala Arg Ala Thr Thr Thr Pro Ala Ser Lys Ser Thr Pro Phe
            980                 985                 990
```

Ser Ile Pro Ser His His Ser Asp Thr Pro Thr Thr Leu Ala Ser His
                995                 1000                1005

Ser Thr Lys Thr Asp Ala Ser Ser Thr His Ser Ser Val Pro
        1010                1015                1020

Pro Leu Thr Ser Ser Asn His Ser Thr Ser Pro Gln Leu Ser Thr
        1025                1030                1035

Gly Val Ser Phe Phe Leu Ser Phe His Ile Ser Asn Leu Gln
        1040                1045                1050

Phe Asn Ser Ser Leu Glu Asp Pro Ser Thr Asp Tyr Tyr Gln Glu
        1055                1060                1065

Leu Gln Arg Asp Ile Ser Glu Met Phe Leu Gln Ile Tyr Lys Gln
        1070                1075                1080

Gly Gly Phe Leu Gly Leu Ser Asn Ile Lys Phe Arg Pro Gly Ser
        1085                1090                1095

Val Val Val Gln Leu Thr Leu Ala Phe Arg Glu Gly Thr Ile Asn
        1100                1105                1110

Val His Asp Val Glu Thr Gln Phe Asn Gln Tyr Lys Thr Glu Ala
        1115                1120                1125

Ala Ser Arg Tyr Asn Leu Thr Ile Ser Asp Val Ser Val Ser Asp
        1130                1135                1140

Val Pro Phe Pro Phe Ser Ala Gln Ser Gly Ala Gly Val Pro Gly
        1145                1150                1155

Trp Gly Ile Ala Leu Leu Val Leu Val Cys Val Leu Val Ala Leu
        1160                1165                1170

Ala Ile Val Tyr Leu Ile Ala Leu Ala Val Cys Gln Cys Arg Arg
        1175                1180                1185

Lys Asn Tyr Gly Gln Leu Asp Ile Phe Pro Ala Arg Asp Thr Tyr
        1190                1195                1200

His Pro Met Ser Glu Tyr Pro Thr Tyr His Thr His Gly Arg Tyr
        1205                1210                1215

Val Pro Pro Ser Ser Thr Asp Arg Ser Pro Tyr Glu Lys Val Ser
        1220                1225                1230

Ala Gly Asn Gly Gly Ser Ser Leu Ser Tyr Thr Asn Pro Ala Val
        1235                1240                1245

Ala Ala Ala Ser Ala Asn Leu
        1250                1255

<210> SEQ ID NO 2
<211> LENGTH: 19
<212> TYPE: PRT
<213> ORGANISM: Artificial Sequence
<220> FEATURE:
<223> OTHER INFORMATION: N-terminal MUC-1 signaling sequence

<400> SEQUENCE: 2

Met Thr Pro Gly Thr Gln Ser Pro Phe Phe Leu Leu Leu Leu Thr
1               5                   10                  15

Val Leu Thr

<210> SEQ ID NO 3
<211> LENGTH: 23
<212> TYPE: PRT
<213> ORGANISM: Artificial Sequence
<220> FEATURE:
<223> OTHER INFORMATION: N-terminal MUC-1 signaling sequence

```
<400> SEQUENCE: 3

Met Thr Pro Gly Thr Gln Ser Pro Phe Phe Leu Leu Leu Leu Leu Thr
1               5                   10                  15

Val Leu Thr Val Val Thr Ala
            20

<210> SEQ ID NO 4
<211> LENGTH: 23
<212> TYPE: PRT
<213> ORGANISM: Artificial Sequence
<220> FEATURE:
<223> OTHER INFORMATION: N-terminal MUC-1 signaling sequence

<400> SEQUENCE: 4

Met Thr Pro Gly Thr Gln Ser Pro Phe Phe Leu Leu Leu Leu Leu Thr
1               5                   10                  15

Val Leu Thr Val Val Thr Gly
            20

<210> SEQ ID NO 5
<211> LENGTH: 146
<212> TYPE: PRT
<213> ORGANISM: Artificial Sequence
<220> FEATURE:
<223> OTHER INFORMATION: A truncated MUC1 receptor isoform

<400> SEQUENCE: 5

Gly Thr Ile Asn Val His Asp Val Glu Thr Gln Phe Asn Gln Tyr Lys
1               5                   10                  15

Thr Glu Ala Ala Ser Arg Tyr Asn Leu Thr Ile Ser Asp Val Ser Val
                20                  25                  30

Ser Asp Val Pro Phe Pro Phe Ser Ala Gln Ser Gly Ala Gly Val Pro
            35                  40                  45

Gly Trp Gly Ile Ala Leu Leu Val Leu Val Cys Val Leu Val Ala Leu
        50                  55                  60

Ala Ile Val Tyr Leu Ile Ala Leu Ala Val Cys Gln Cys Arg Arg Lys
65                  70                  75                  80

Asn Tyr Gly Gln Leu Asp Ile Phe Pro Ala Arg Asp Thr Tyr His Pro
                85                  90                  95

Met Ser Glu Tyr Pro Thr Tyr His Thr His Gly Arg Tyr Val Pro Pro
            100                 105                 110

Ser Ser Thr Asp Arg Ser Pro Tyr Glu Lys Val Ser Ala Gly Asn Gly
        115                 120                 125

Gly Ser Ser Leu Ser Tyr Thr Asn Pro Ala Val Ala Ala Ala Ser Ala
130                 135                 140

Asn Leu
145

<210> SEQ ID NO 6
<211> LENGTH: 171
<212> TYPE: PRT
<213> ORGANISM: Artificial Sequence
<220> FEATURE:
<223> OTHER INFORMATION: A truncated MUC1 receptor isoform

<400> SEQUENCE: 6

Gly Phe Leu Gly Leu Ser Asn Ile Lys Phe Arg Pro Gly Ser Val Val
1               5                   10                  15

Val Gln Leu Thr Leu Ala Phe Arg Glu Gly Thr Ile Asn Val His Asp
            20                  25                  30
```

Val Glu Thr Gln Phe Asn Gln Tyr Lys Thr Glu Ala Ala Ser Arg Tyr
            35                  40                  45

Asn Leu Thr Ile Ser Asp Val Ser Val Ser Asp Val Pro Phe Pro Phe
 50                  55                  60

Ser Ala Gln Ser Gly Ala Gly Val Pro Gly Trp Gly Ile Ala Leu Leu
 65                  70                  75                  80

Val Leu Val Cys Val Leu Val Ala Leu Ala Ile Val Tyr Leu Ile Ala
                 85                  90                  95

Leu Ala Val Cys Gln Cys Arg Arg Lys Asn Tyr Gly Gln Leu Asp Ile
                100                 105                 110

Phe Pro Ala Arg Asp Thr Tyr His Pro Met Ser Glu Tyr Pro Thr Tyr
            115                 120                 125

His Thr His Gly Arg Tyr Val Pro Pro Ser Ser Thr Asp Arg Ser Pro
130                 135                 140

Tyr Glu Lys Val Ser Ala Gly Asn Gly Gly Ser Ser Leu Ser Tyr Thr
145                 150                 155                 160

Asn Pro Ala Val Ala Ala Ala Ser Ala Asn Leu
                165                 170

<210> SEQ ID NO 7
<211> LENGTH: 275
<212> TYPE: PRT
<213> ORGANISM: Artificial Sequence
<220> FEATURE:
<223> OTHER INFORMATION: A truncated MUC1 receptor isoform

<400> SEQUENCE: 7

Ala Thr Thr Thr Pro Ala Ser Lys Ser Thr Pro Phe Ser Ile Pro Ser
 1               5                  10                  15

His His Ser Asp Thr Pro Thr Thr Leu Ala Ser His Ser Thr Lys Thr
                 20                  25                  30

Asp Ala Ser Ser Thr His His Ser Thr Val Pro Pro Leu Thr Ser Ser
             35                  40                  45

Asn His Ser Thr Ser Pro Gln Leu Ser Thr Gly Val Ser Phe Phe Phe
 50                  55                  60

Leu Ser Phe His Ile Ser Asn Leu Gln Phe Asn Ser Ser Leu Glu Asp
 65                  70                  75                  80

Pro Ser Thr Asp Tyr Tyr Gln Glu Leu Gln Arg Asp Ile Ser Glu Met
                 85                  90                  95

Phe Leu Gln Ile Tyr Lys Gln Gly Gly Phe Leu Gly Leu Ser Asn Ile
                100                 105                 110

Lys Phe Arg Pro Gly Ser Val Val Val Gln Leu Thr Leu Ala Phe Arg
            115                 120                 125

Glu Gly Thr Ile Asn Val His Asp Val Glu Thr Gln Phe Asn Gln Tyr
130                 135                 140

Lys Thr Glu Ala Ala Ser Arg Tyr Asn Leu Thr Ile Ser Asp Val Ser
145                 150                 155                 160

Val Ser Asp Val Pro Phe Pro Phe Ser Ala Gln Ser Gly Ala Gly Val
                165                 170                 175

Pro Gly Trp Gly Ile Ala Leu Leu Val Leu Val Cys Val Leu Val Ala
            180                 185                 190

Leu Ala Ile Val Tyr Leu Ile Ala Leu Ala Val Cys Gln Cys Arg Arg
        195                 200                 205

Lys Asn Tyr Gly Gln Leu Asp Ile Phe Pro Ala Arg Asp Thr Tyr His
210                 215                 220

Pro Met Ser Glu Tyr Pro Thr Tyr His Thr His Gly Arg Tyr Val Pro
225                 230                 235                 240

Pro Ser Ser Thr Asp Arg Ser Pro Tyr Glu Lys Val Ser Ala Gly Asn
            245                 250                 255

Gly Gly Ser Ser Leu Ser Tyr Thr Asn Pro Ala Val Ala Ala Ala Ser
            260                 265                 270

Ala Asn Leu
        275

<210> SEQ ID NO 8
<211> LENGTH: 233
<212> TYPE: PRT
<213> ORGANISM: Artificial Sequence
<220> FEATURE:
<223> OTHER INFORMATION: A truncated MUC1 receptor isoform

<400> SEQUENCE: 8

Gly Ser Gly His Ala Ser Ser Thr Pro Gly Gly Glu Lys Glu Thr Ser
1               5                   10                  15

Ala Thr Gln Arg Ser Ser Val Pro Ser Ser Thr Glu Lys Asn Ala Phe
            20                  25                  30

Asn Ser Ser Leu Glu Asp Pro Ser Thr Asp Tyr Tyr Gln Glu Leu Gln
        35                  40                  45

Arg Asp Ile Ser Glu Met Phe Leu Gln Ile Tyr Lys Gln Gly Gly Phe
50                  55                  60

Leu Gly Leu Ser Asn Ile Lys Phe Arg Pro Gly Ser Val Val Val Gln
65                  70                  75                  80

Leu Thr Leu Ala Phe Arg Glu Gly Thr Ile Asn Val His Asp Met Glu
                85                  90                  95

Thr Gln Phe Asn Gln Tyr Lys Thr Glu Ala Ala Ser Arg Tyr Asn Leu
            100                 105                 110

Thr Ile Ser Asp Val Ser Val Ser Asp Val Pro Phe Pro Phe Ser Ala
        115                 120                 125

Gln Ser Gly Ala Gly Val Pro Gly Trp Gly Ile Ala Leu Leu Val Leu
130                 135                 140

Val Cys Val Leu Val Ala Leu Ala Ile Val Tyr Leu Ile Ala Leu Ala
145                 150                 155                 160

Val Cys Gln Cys Arg Arg Lys Asn Tyr Gly Gln Leu Asp Ile Phe Pro
                165                 170                 175

Ala Arg Asp Thr Tyr His Pro Met Ser Glu Tyr Pro Thr Tyr His Thr
            180                 185                 190

His Gly Arg Tyr Val Pro Pro Ser Ser Thr Asp Arg Ser Pro Tyr Glu
        195                 200                 205

Lys Val Ser Ala Gly Asn Gly Gly Ser Ser Leu Ser Tyr Thr Asn Pro
210                 215                 220

Ala Val Ala Ala Thr Ser Ala Asn Leu
225                 230

<210> SEQ ID NO 9
<211> LENGTH: 863
<212> TYPE: PRT
<213> ORGANISM: Artificial Sequence
<220> FEATURE:
<223> OTHER INFORMATION: A truncated MUC1 receptor isoform

<400> SEQUENCE: 9

```
Leu Asp Pro Arg Val Arg Thr Ser Ala Pro Asp Thr Arg Pro Ala Pro
1               5                   10                  15
Gly Ser Thr Ala Pro Gln Ala His Gly Val Thr Ser Ala Pro Asp Thr
            20                  25                  30
Arg Pro Ala Pro Gly Ser Thr Ala Pro Pro Ala His Gly Val Thr Ser
            35                  40                  45
Ala Pro Asp Thr Arg Pro Ala Pro Gly Ser Thr Ala Pro Pro Ala His
        50                  55                  60
Gly Val Thr Ser Ala Pro Asp Thr Arg Pro Ala Pro Gly Ser Thr Ala
65                  70                  75                  80
Pro Pro Ala His Gly Val Thr Ser Ala Pro Asp Thr Arg Pro Ala Pro
                85                  90                  95
Gly Ser Thr Ala Pro Pro Ala His Gly Val Thr Ser Ala Pro Asp Thr
            100                 105                 110
Arg Pro Ala Pro Gly Ser Thr Ala Pro Pro Ala His Gly Val Thr Ser
            115                 120                 125
Ala Pro Asp Thr Arg Pro Ala Pro Gly Ser Thr Ala Pro Pro Ala His
        130                 135                 140
Gly Val Thr Ser Ala Pro Asp Thr Arg Pro Ala Pro Gly Ser Thr Ala
145                 150                 155                 160
Pro Pro Ala His Gly Val Thr Ser Ala Pro Asp Thr Arg Pro Ala Pro
                165                 170                 175
Gly Ser Thr Ala Pro Pro Ala His Gly Val Thr Ser Ala Pro Asp Thr
            180                 185                 190
Arg Pro Ala Pro Gly Ser Thr Ala Pro Pro Ala His Gly Val Thr Ser
            195                 200                 205
Ala Pro Asp Thr Arg Pro Ala Pro Gly Ser Thr Ala Pro Pro Ala His
        210                 215                 220
Gly Val Thr Ser Ala Pro Asp Thr Arg Pro Ala Pro Gly Ser Thr Ala
225                 230                 235                 240
Pro Pro Ala His Gly Val Thr Ser Ala Pro Asp Thr Arg Pro Ala Pro
                245                 250                 255
Gly Ser Thr Ala Pro Pro Ala His Gly Val Thr Ser Ala Pro Asp Thr
            260                 265                 270
Arg Pro Ala Pro Gly Ser Thr Ala Pro Pro Ala His Gly Val Thr Ser
            275                 280                 285
Ala Pro Asp Thr Arg Pro Ala Pro Gly Ser Thr Ala Pro Pro Ala His
        290                 295                 300
Gly Val Thr Ser Ala Pro Asp Thr Arg Pro Ala Pro Gly Ser Thr Ala
305                 310                 315                 320
Pro Pro Ala His Gly Val Thr Ser Ala Pro Asp Thr Arg Pro Ala Pro
                325                 330                 335
Gly Ser Thr Ala Pro Pro Ala His Gly Val Thr Ser Ala Pro Asp Thr
            340                 345                 350
Arg Pro Ala Pro Gly Ser Thr Ala Pro Pro Ala His Gly Val Thr Ser
            355                 360                 365
Ala Pro Asp Thr Arg Pro Ala Pro Gly Ser Thr Ala Pro Pro Ala His
        370                 375                 380
Gly Val Thr Ser Ala Pro Asp Thr Arg Pro Ala Pro Gly Ser Thr Ala
385                 390                 395                 400
Pro Pro Ala His Gly Val Thr Ser Ala Pro Asp Thr Arg Pro Ala Pro
                405                 410                 415
```

```
Gly Ser Thr Ala Pro Pro Ala His Gly Val Thr Ser Ala Pro Asp Thr
            420             425             430
Arg Pro Ala Pro Gly Ser Thr Ala Pro Pro Ala His Gly Val Thr Ser
            435             440             445
Ala Pro Asp Thr Arg Pro Ala Pro Gly Ser Thr Ala Pro Pro Ala His
            450             455             460
Gly Val Thr Ser Ala Pro Asp Thr Arg Pro Ala Pro Gly Ser Thr Ala
465             470             475             480
Pro Pro Ala His Gly Val Thr Ser Ala Pro Asp Thr Arg Pro Ala Pro
            485             490             495
Gly Ser Thr Ala Pro Pro Ala His Gly Val Thr Ser Ala Pro Asp Thr
            500             505             510
Arg Pro Ala Pro Gly Ser Thr Ala Pro Pro Ala His Gly Val Thr Ser
            515             520             525
Ala Pro Asp Thr Arg Pro Ala Pro Gly Ser Thr Ala Pro Pro Ala His
            530             535             540
Gly Val Thr Ser Ala Pro Asp Asn Arg Pro Ala Leu Gly Ser Thr Ala
545             550             555             560
Pro Pro Val His Asn Val Thr Ser Ala Ser Gly Ser Ala Ser Gly Ser
            565             570             575
Ala Ser Thr Leu Val His Asn Gly Thr Ser Ala Arg Ala Thr Thr Thr
            580             585             590
Pro Ala Ser Lys Ser Thr Pro Phe Ser Ile Pro Ser His His Ser Asp
            595             600             605
Thr Pro Thr Thr Leu Ala Ser His Ser Thr Lys Thr Asp Ala Ser Ser
            610             615             620
Thr His His Ser Ser Val Pro Pro Leu Thr Ser Ser Asn His Ser Thr
625             630             635             640
Ser Pro Gln Leu Ser Thr Gly Val Ser Phe Phe Leu Ser Phe His
            645             650             655
Ile Ser Asn Leu Gln Phe Asn Ser Ser Leu Glu Asp Pro Ser Thr Asp
            660             665             670
Tyr Tyr Gln Glu Leu Gln Arg Asp Ile Ser Glu Met Phe Leu Gln Ile
            675             680             685
Tyr Lys Gln Gly Gly Phe Leu Gly Leu Ser Asn Ile Lys Phe Arg Pro
            690             695             700
Gly Ser Val Val Val Gln Leu Thr Leu Ala Phe Arg Glu Gly Thr Ile
705             710             715             720
Asn Val His Asp Val Glu Thr Gln Phe Asn Gln Tyr Lys Thr Glu Ala
            725             730             735
Ala Ser Arg Tyr Asn Leu Thr Ile Ser Asp Val Ser Val Ser Asp Val
            740             745             750
Pro Phe Pro Phe Ser Ala Gln Ser Gly Ala Gly Val Pro Gly Trp Gly
            755             760             765
Ile Ala Leu Leu Val Leu Val Cys Val Leu Val Ala Leu Ala Ile Val
            770             775             780
Tyr Leu Ile Ala Leu Ala Val Cys Gln Cys Arg Arg Lys Asn Tyr Gly
785             790             795             800
Gln Leu Asp Ile Phe Pro Ala Arg Asp Thr Tyr His Pro Met Ser Glu
            805             810             815
Tyr Pro Thr Tyr His Thr His Gly Arg Tyr Val Pro Pro Ser Ser Thr
            820             825             830
```

Asp Arg Ser Pro Tyr Glu Lys Val Ser Ala Gly Asn Gly Gly Ser Ser
        835                 840                 845

Leu Ser Tyr Thr Asn Pro Ala Val Ala Ala Ala Ser Ala Asn Leu
    850                 855                 860

<210> SEQ ID NO 10
<211> LENGTH: 45
<212> TYPE: PRT
<213> ORGANISM: Artificial Sequence
<220> FEATURE:
<223> OTHER INFORMATION: Native Primary Sequence

<400> SEQUENCE: 10

Gly Thr Ile Asn Val His Asp Val Glu Thr Gln Phe Asn Gln Tyr Lys
1               5                   10                  15

Thr Glu Ala Ala Ser Arg Tyr Asn Leu Thr Ile Ser Asp Val Ser Val
            20                  25                  30

Ser Asp Val Pro Phe Pro Phe Ser Ala Gln Ser Gly Ala
        35                  40                  45

<210> SEQ ID NO 11
<211> LENGTH: 44
<212> TYPE: PRT
<213> ORGANISM: Artificial Sequence
<220> FEATURE:
<223> OTHER INFORMATION: Native Primary Sequence

<400> SEQUENCE: 11

Thr Ile Asn Val His Asp Val Glu Thr Gln Phe Asn Gln Tyr Lys Thr
1               5                   10                  15

Glu Ala Ala Ser Arg Tyr Asn Leu Thr Ile Ser Asp Val Ser Val Ser
            20                  25                  30

Asp Val Pro Phe Pro Phe Ser Ala Gln Ser Gly Ala
        35                  40

<210> SEQ ID NO 12
<211> LENGTH: 45
<212> TYPE: PRT
<213> ORGANISM: Artificial Sequence
<220> FEATURE:
<223> OTHER INFORMATION: "SPY" functional variant

<400> SEQUENCE: 12

Gly Thr Ile Asn Val His Asp Val Glu Thr Gln Phe Asn Gln Tyr Lys
1               5                   10                  15

Thr Glu Ala Ala Ser Pro Tyr Asn Leu Thr Ile Ser Asp Val Ser Val
            20                  25                  30

Ser Asp Val Pro Phe Pro Phe Ser Ala Gln Ser Gly Ala
        35                  40                  45

<210> SEQ ID NO 13
<211> LENGTH: 44
<212> TYPE: PRT
<213> ORGANISM: Artificial Sequence
<220> FEATURE:
<223> OTHER INFORMATION: "SPY" functional variant

```
<400> SEQUENCE: 13

Thr Ile Asn Val His Asp Val Glu Thr Gln Phe Asn Gln Tyr Lys Thr
1               5                   10                  15

Glu Ala Ala Ser Pro Tyr Asn Leu Thr Ile Ser Asp Val Ser Val Ser
            20                  25                  30

Asp Val Pro Phe Pro Phe Ser Ala Gln Ser Gly Ala
        35                  40

<210> SEQ ID NO 14
<211> LENGTH: 33
<212> TYPE: PRT
<213> ORGANISM: Artificial Sequence
<220> FEATURE:
<223> OTHER INFORMATION: Truncated PSMGFR receptor

<400> SEQUENCE: 14

Gly Thr Ile Asn Val His Asp Val Glu Thr Gln Phe Asn Gln Tyr Lys
1               5                   10                  15

Thr Glu Ala Ala Ser Pro Tyr Asn Leu Thr Ile Ser Asp Val Ser Val
            20                  25                  30

Ser

<210> SEQ ID NO 15
<211> LENGTH: 48
<212> TYPE: PRT
<213> ORGANISM: Artificial Sequence
<220> FEATURE:
<223> OTHER INFORMATION: Extended Sequence

<400> SEQUENCE: 15

Val Gln Leu Thr Leu Ala Phe Arg Glu Gly Thr Ile Asn Val His Asp
1               5                   10                  15

Val Glu Thr Gln Phe Asn Gln Tyr Lys Thr Glu Ala Ala Ser Pro Tyr
            20                  25                  30

Asn Leu Thr Ile Ser Asp Val Ser Val Ser Asp Val Pro Phe Pro Phe
        35                  40                  45

<210> SEQ ID NO 16
<211> LENGTH: 57
<212> TYPE: PRT
<213> ORGANISM: Artificial Sequence
<220> FEATURE:
<223> OTHER INFORMATION: Tumor-Specific Extended Sequence

<400> SEQUENCE: 16

Ser Val Val Val Gln Leu Thr Leu Ala Phe Arg Glu Gly Thr Ile Asn
1               5                   10                  15

Val His Asp Val Glu Thr Gln Phe Asn Gln Tyr Lys Thr Glu Ala Ala
            20                  25                  30

Ser Pro Tyr Asn Leu Thr Ile Ser Asp Val Ser Val Ser Asp Val Pro
        35                  40                  45

Phe Pro Phe Ser Ala Gln Ser Gly Ala
    50                  55

<210> SEQ ID NO 17
<211> LENGTH: 25
<212> TYPE: PRT
<213> ORGANISM: Artificial Sequence
<220> FEATURE:
<223> OTHER INFORMATION: Primary Sequence
```

```
<400> SEQUENCE: 17

Gly Phe Leu Gly Leu Ser Asn Ile Lys Phe Arg Pro Gly Ser Val Val
1               5                   10                  15

Val Gln Leu Thr Leu Ala Phe Arg Glu
            20                  25

<210> SEQ ID NO 18
<211> LENGTH: 13
<212> TYPE: PRT
<213> ORGANISM: Artificial Sequence
<220> FEATURE:
<223> OTHER INFORMATION: Truncated Interchain

<400> SEQUENCE: 18

Ser Val Val Val Gln Leu Thr Leu Ala Phe Arg Glu Gly
1               5                   10

<210> SEQ ID NO 19
<211> LENGTH: 40
<212> TYPE: PRT
<213> ORGANISM: Artificial Sequence
<220> FEATURE:
<223> OTHER INFORMATION: Repeat Motif 2

<400> SEQUENCE: 19

Pro Asp Thr Arg Pro Ala Pro Gly Ser Thr Ala Pro Pro Ala His Gly
1               5                   10                  15

Val Thr Ser Ala Pro Asp Thr Arg Pro Ala Pro Gly Ser Thr Ala Pro
            20                  25                  30

Pro Ala His Gly Val Thr Ser Ala
            35                  40
```